(12) United States Patent
Mukai et al.

(10) Patent No.: US 7,285,618 B1
(45) Date of Patent: Oct. 23, 2007

(54) POLYPEPTIDES HAVING NEUTROPHIL STIMULATING ACTIVITY

(75) Inventors: Hidehito Mukai, Kanagawa (JP); Yoshisuke Nishi, Kanagawa (JP); Eisuke Munekata, Ibaraki (JP)

(73) Assignee: Japan Tobacco Inc., Tokyo (JP)

( * ) Notice: Subject to any disclaimer, the term of this patent is extended or adjusted under 35 U.S.C. 154(b) by 440 days.

(21) Appl. No.: 10/220,849

(22) PCT Filed: Mar. 6, 2001

(86) PCT No.: PCT/JP01/01729

§ 371 (c)(1),
(2), (4) Date: Sep. 6, 2002

(87) PCT Pub. No.: WO01/66734

PCT Pub. Date: Sep. 13, 2001

(30) Foreign Application Priority Data

Mar. 7, 2000 (JP) .............................. 2000-062045

(51) Int. Cl.
*C07K 4/12* (2006.01)
*A61K 38/00* (2006.01)
(52) U.S. Cl. ........................................ 530/300; 930/10
(58) Field of Classification Search ................ 530/300; 514/13
See application file for complete search history.

(56) References Cited

FOREIGN PATENT DOCUMENTS

| EP | 538030 A2 | 4/1993 |
|---|---|---|
| JP | 8-20600 A | 1/1996 |
| WO | 90/06321 A1 | 6/1990 |

OTHER PUBLICATIONS

Lazar et al (Molecualr and Cell Biology, vol. 8, No. 3, pp. 1247-1252, 1988.*
Lightowlers et al, Dataase PIR: Accession No. A35537; Spurr et al. Database PIR: Accession No. AAA31851.*
Rizzuto et al. Database PIR: Accession No. P10176.*
Lin et al. Database PIR: Accession No. AAA31851.*
Rambhav, S. Journal of Bioscience, vol. 3, No. 3, Sep. 1981, pp. 221-226.*
Eckhard K. et al., "Production of superoxide anion and hydrogen peroxide by human neutrophilic granulocytes", vol. 93, No. 4, pp. 344-349, (1990).
Takato T. et al., β-Amyloid peptide, substance P, and SEC receptor ligand activate cytoplasmic $Ca^2$ . . . , Peptides, vol .16, No. 6, pp. 1019-1024, (1995).
Ehlert J.E. et al. "The Journal of Immunology" 1998, vol. 161, pp. 4975-4982.
H. Mukai et al., "Inflammatory activation of neutrophils triggered by a novel class of peptides" in Vitro Cellular and Developmental Biology Animal, vol. 36, No. 3, Part 2, Mar. 2000, p. 52.A, XP002329800 and Meeting for the Society for in Vitro Biology World Congress on in Vitro Biology, San Diego, California, USA; Jun. 10-15, 2000 ISSN: 1071-2690 *abstract*.

* cited by examiner

*Primary Examiner*—Eileen B. O'Hara
*Assistant Examiner*—Fozia Hamud
(74) *Attorney, Agent, or Firm*—Birch, Stewart, Kolasch & Birch, LLP

(57) ABSTRACT

Neutrophil attracting and activating factors that may already exist in normal cells are located.

Polypeptides having neutrophil stimulating activity were isolated from an extract originating from a normal porcine heart, whereby the invention was completed. The invention provides (a) a polypeptide consisting of the amino acid sequence of SEQ ID NO:1; (b) a polypeptide consisting of an amino acid sequence derived from the amino acid sequence of SEQ ID NO:3 by deletion, substitution, insertion or addition of one or more amino acids and having neutrophil stimulating activity; or (c) a polypeptide consisting of an amino acid sequence biologically equivalent to the amino acid sequence of said polypeptide (a) or (b).

14 Claims, 10 Drawing Sheets

POLYPEPTIDES HAVING NEUTROPHIL STIMULATING ACTIVITY

This application is the national phase under 35 U.S.C. § 371 of PCT International Application No. PCT/JP01/01729 which has an International filing date of Mar. 6, 2001, which designated the United States of America.

TECHNICAL FIELD

This invention relates to polypeptides having neutrophil stimulating (migrating or activating) activity. The polypeptides of the invention and their receptors, as well as antibodies against them, can be used in the treatment, diagnosis, etc. of diseases or conditions associated with neutrophil stimulation.

BACKGROUND ART

Inflammations are complex reactions characterized by interactions between a variety of factors, which are mainly associated with leukocytes. Inflammatory stimuli cause migration of leukocytes to a site of stimulation via venules. In acute inflammation, neutrophils first infiltrate such a site and infiltration by macrophages and lymphocytes follows. Depending on the type of inflammation, infiltration of eosinophils and basophils also occurs. Infiltration between these leukocytes varies depending on the type of inflammation and so does the duration of infiltration; hence, different mechanisms have been proposed for the respective leukocytes.

The infiltration of neutrophils is also a complex phenomenon. It is said that, neutrophils normally flow in the center of the blood stream. But when a stimulus is exerted, it causes an increase in the microcirculation and a decrease in the rate of blood flow, thereby the neutrophils reach to the blood vessel wall and flow there in accordance with the mechanism of fluid dynamics, eventually coming into contact with vascular endothelium. At the early stage, neutrophils roll over and move slowly, as if they walk along the surface of endothelial cells. Then, they adhere (bind) firmly to the endothelial cells. The adherent neutrophils extrude pseudopodia toward the site where they bind to endothelial cells and the endothelial cells also surround the neutrophils. The neutrophils then extend toward the subendothelial cavity, pass through the vascular adventitial (perithelial) cells, and finally infiltrate into the tissues. At a site where the inflammatory stimulative foreign body exists, neutrophils exhibit their functions, through production of active oxygen, secretion of degradative infiltration enzymes, release of cytokines and phagocytosis.

The infiltration of neutrophils is not limited to the case of invasion of foreign bodies, such as viruses and bacteria. At the time myocardial infarction or an organ transplant occurs and, the blood flow into the organ is recovered, organ injuries accompanied by the infiltration of neutrophils sometimes occur. This symptom is called 'ischemic reperfusion injury'.

Neutrophils are considered to respond to the chemotactic factors, which are produced at a site of inflammation, and move to the site by recognizing the density gradients of those factors. Factors (chemotactic factors) known to date are capable of inducing the migration of neutrophils to a local site. They are a series of proteinaceous factors called 'chemokines', 'complement factors C3a and C5a', a factor in the metabolism of arachiodonic acid 'leukotriene $B_4$', and other factors, such as 'platelet-activating factors' and formyl peptides including formyl methionyl-leucyl-phenylalanine (fMLF), which is a model peptide of bacterial proteins (Annu. Rev. Immunol. 2, 257-281, 1984 and Annu. Rev. Immunol. 15, 675-705, 1997). However, it is not completely clear how these substances are involved at the stage of inflammation.

'Chemokine(s)' are the collective term for proteinaceous endogenous substances that are capable of causing neutrophils, monocytes, T lymphocytes, etc. to migrate to local sites. 'Chemokines' are classified into four families according to their primary structures, including a CC family (1), in which the first and second cysteine residues from the N terminus are aligned adjacent to each other, a CXC family (2), in which the two cysteine residues are separated by one amino acid, a $CX_3C$ family (3), in which the two cysteine residues are interrupted by three amino acids, and a C family (4), having one cysteine residue. Among these families, only the CXC family is considered to act on neutrophils and chemokines known to belong to this family include interleukin-8 (IL-8), neutrophil activating protein-2, etc. (Annu. Rev. Immunol. 15, 675-705, 1997).

It is also known that at the site of inflammation, the active oxygen, degradative enzymes and other substances that are released by activated neutrophils cause the cell injury. Since the concentrations of various chemokines including IL-8 are elevated in the tissues affected by such injuries, it is said that IL-8 and other chemokines are also involved in the tissue destruction by the activated neutrophils. However, it is hard to believe that IL-8 is involved at the stage where the cell injury occurs.

DISCLOSURE OF THE INVENTION

Chemokines do not always exist in the normal tissue and they are considered to be synthesized when a certain stimulus is given to the tissue and to exhibit their functions after they are secreted. It is generally accepted that transcription and translation of genes to express proteins require from several hours to about half a day. In contrast, the actual inflammatory reaction often appears earlier. Therefore, it is possible that factors attracting and activating neutrophils may already exist in the normal cells. Discovering these factors could lead to the establishment of a method for suppressing the onset of inflammations at the early stage, thus proving extremely useful in the development of drugs for diagnosis and treatment of various tissue inflammations including inflammatory diseases, such as 'rheumatism', 'acute nephritis' and 'fulminant hepatitis', and 'ischemic reperfusion injury'.

The present inventors conducted various studies in a view of finding 'factors' that cause the neutrophil stimulation (migration and activation), and they are previously prepared in the normal cells. As a result, they isolated a novel polypeptide having neutrophil stimulating activity (SEQ ID NO:1) from an extract originating from a normal porcine heart and also isolated various novel polypeptides (SEQ ID NO: 3, 4 and 5) that were predicted to have similar activity to this novel polypeptide. The present inventors also found the possibility that those novel polypeptides would activate G proteins either directly or via novel receptors. The present inventors further found the possibility that those novel polypeptides would have a novel characteristic such that they have the activity to permit the neutrophils to migrate at a certain concentration, but that as their concentration increased, the migrating activity was desensitized and activating the neutrophils were emerged (secretion of degradative enzymes, production of various cytokines and perox-

DETAILED DESCRIPTION OF THE INVENTION

Figure 1:
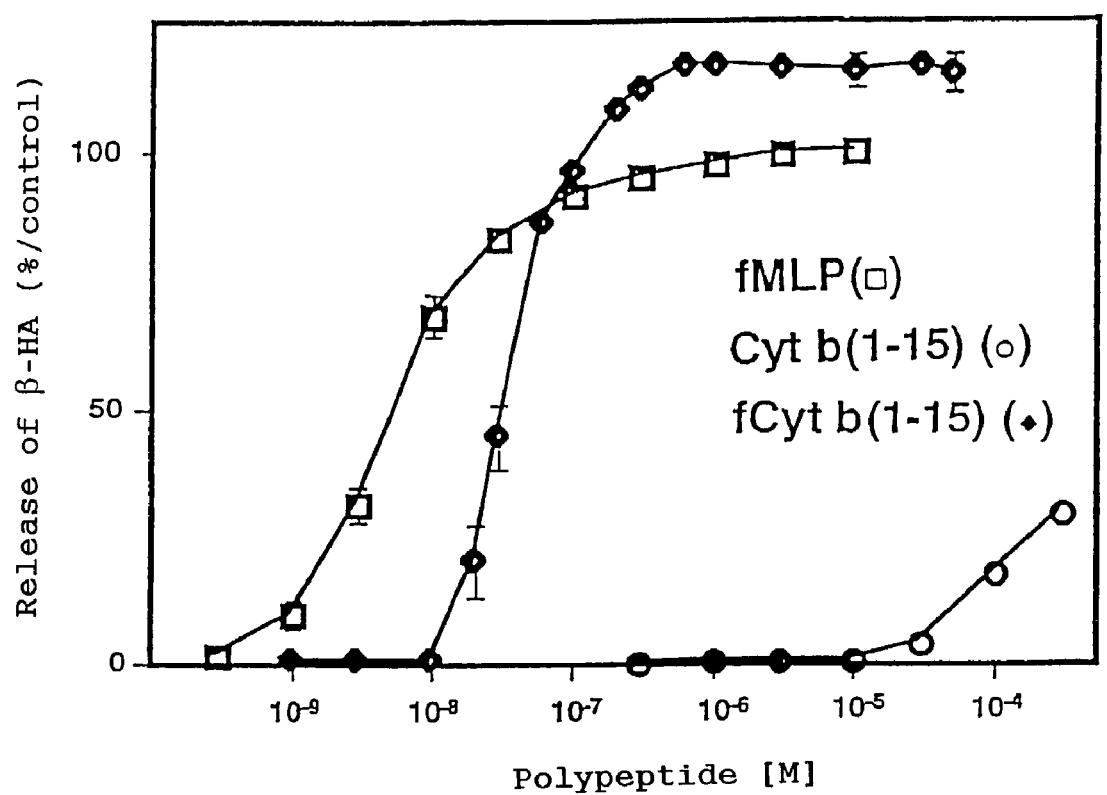
FIG. 1 shows the results of experiments on the activity of polypeptides in inducing β-HA secretion from differentiated HL60 cells (Example 4). The data show the mean±S.E. for 8 different experiments [□, fMLP; ○, Cyt b (1-15); ◇, fCyt b (1-15)]

Polypeptides having a Stimulating Activity of Neutrophils

The present invention provides (a) a polypeptide consisting of the amino acid sequence of SEQ ID NO:1; (b) a polypeptide consisting of an amino acid sequence derived from the amino acid sequence of SEQ ID NO:1 by deletion, substitution, insertion or addition of one or more amino acids and having neutrophil stimulating activity; or (c) a polypeptide consisting of an amino acid sequence biologically equivalent to the amino acid sequence of said polypeptide (a) or (b). The present invention also provides (a) a polypeptide consisting of the amino acid sequence of SEQ ID NO:3; (b) a polypeptide consisting of an amino acid sequence derived from the amino acid sequence of SEQ ID NO:3 by deletion, substitution, insertion or addition of one or more amino acids and having neutrophil stimulating activity; or (c) a polypeptide consisting of an amino acid sequence biologically equivalent to the amino acid sequence of said polypeptide (a) or (b). The present invention also provides (a) a polypeptide consisting of the amino acid sequence of SEQ ID NO:4; (b) a polypeptide consisting of an amino acid sequence derived from the amino acid sequence of SEQ ID NO:4 by deletion, substitution, insertion or addition of one or more amino acids and having neutrophil stimulating activity; or (c) a polypeptide consisting of an amino acid sequence biologically equivalent to the amino acid sequence of said polypeptide (a) or (b). And the present invention also provides (a) a polypeptide consisting of the amino acid sequence of SEQ ID NO:5; (b) a polypeptide consisting of an amino acid sequence derived from the amino acid sequence of SEQ ID NO:5 by deletion, substitution, insertion or addition of one or more amino acids and having neutrophil stimulating activity; or (c) a polypeptide consisting of an amino acid sequence biologically equivalent to the amino acid sequence of said polypeptide (a) or (b).

The polypeptide of SEQ ID NO:1 has 23 amino acid residues but does not contain a cysteine residue. This polypeptide is 82% homologous to the 23 residues (SEQ ID NO:2) of the C terminal of bovine heart cytochrome C oxidase subunit VIII (19 out of the 23 residues are identical). Further, this polypeptide is 57% homologous to the 21 residues (SEQ ID NO:3) of the C terminal of human cytochrome C oxidase subunit VIII (12 out of the 21 residues are identical).

SEQ ID NO:1, Leu-Ser-Phe-Leu-Ile-Pro-Ala-Gly-Trp-Val-Leu-Ser-His-Leu-Asp-His-Tyr-Lys-Arg-Ser-Ser-Ala-Ala

SEQ ID NO:2, Leu-Ser-Phe-Leu-Leu-Pro-Ala-Gly-Trp-Val-Leu-Tyr-His-Leu-Asp-Asn-Tyr-Lys-Lys-Ser-Ser-Ala-Ala

SEQ ID NO:3, Val-Thr-Phe-Leu-Leu-Pro-Ala-Gly-Trp-Ile-Leu-Ser-His-Leu-Glu-Thr-Tyr-Arg-Arg-Pro-Glu

In this specification, the polypeptide of SEQ ID NO:1 is sometimes referred to as COSP-1.

The polypeptide of SEQ ID NO:4 has a sequence that is identical to that of swine cytochrome b (1-15) and which consists of the following 15 amino acid residues. In this specification, this peptide is sometimes referred to as fCyt b (1-15). This is 67% homologous to human cytochrome b (1-15) (SEQ ID NO:5) (10 out of the 15 residues are identical).

SEQ ID NO:4, fMet-Thr-Asn-Ile-Arg-Lys-Ser-His-Pro-Leu-Met-Lys-Ile-Ile-Asn

SEQ ID NO:5, fMet-Thr-Pro-Met-Arg-Lys-Ile-Asn-Pro-Leu-Met-Lys-Leu-Ile-Asn

In these sequences, fMet represents a formyl methionyl residue.

The term "neutrophils" as used herein covers not only neutrophils but also neutrophil-like cells in animals including man. A specific example of neutrophil-like cells is the HL60 cells differentiated after treatment with dibutyric cyclic AMP. The term "neutrophil stimulating activity" means the activity of promoting the migration (sometimes referred to as "chemotaxis") and/or activation of neutrophils or neutrophil-like cells in animals including man. Migration covers infiltration of neutrophils or neutrophil-like cells into a tissue and their movement to a local site. Activation covers the production of active oxygen, secretion of degradative enzymes (e.g. β-HA), production of various cytokines and peroxides, as well as phagocytosis. These neutrophil stimulating activities can be assayed by measuring chemotactic activity of the neutrophil, release of active oxygen, and measuring the amount of β-HA secretion and/or the elevation of intracellular $Ca^{2+}$ concentration. When it is stated in this specification that a certain polypeptide "has neutrophil stimulating activity", the neutrophil stimulating activity of interest may be either the activity of promoting the migration of neutrophils or the activity of promoting the activation of neutrophils or both activities.

Referring to the expression "an amino acid sequence derived by deletion, substitution, insertion or addition of one or more amino acids" as used in this specification, the number of amino acids involved is not limited in any particular way as long as the polypeptide composed of the amino acid sequence in question has neutrophil stimulating activity and the substitutions engineered the well-known technical methods such as site-directed mutagenesis or the substitution of as many amino acids as that can occur naturally are included. The activity of interest would not be lost if about 1-9 or 1-4 of amino acids are deleted, substituted, inserted or added. Further, referring to the expression "an amino acid sequence derived from the amino acid sequence of SEQ ID NO:x by deletion, substitution, insertion or addition of one or more amino" as used in this specification, the amino acid sequence in question includes those amino acid sequences which are homologous to the amino acid sequence of SEQ ID NO:x. The homology should be at least 50%, preferably at least 60%, more preferably at least 70%, further preferably at least 80%, still further preferably at least 90%, yet more preferably at least 95%, and most preferably at least 98%. The term "homologous" or "homology" as used herein means the degree by which the amino acid residues composing one sequence are similar to those composing another sequence to be compared. In this case, the presence of gaps and the properties of amino acids are taken into consideration. To calculate homology, commercially available software packages may be employed.

In addition, referring to the expression "an amino acid sequence biologically equivalent" to the amino acid sequence of a certain polypeptide as used in this specification, the amino acid sequence of interest means one that is identical to the amino acid sequence of said polypeptide which contains modified amino acids but which has comparable functions and actions (e.g. neutrophil stimulating activity) to said polypeptide. Modification can occur at the N terminus (amino group) or C terminus (carboxyl group) of a polypeptide, as well as in other groups in the amino acid side chains. Exemplary modifications include formulation, acetylation or methylation of the N terminus, esterification or amidation of the C terminus, and others. Formylation of the N terminus is particularly preferred.

The polypeptides of the invention can be prepared from animal tissue materials. Procedures for preparation may be conventional methods for purifying peptide components from animal tissue materials (e.g. affinity chromatography, ion-exchange chromatography, gel filtration and HPLC). For instance, a fraction having neutrophil stimulating activity can be obtained by fractionation of a crude peptide extract from a porcine heart homogenate. The polypeptides of the invention can also be obtained by chemical synthesis. Synthesis can be performed by using conventional methods for polypeptide synthesis. Examples of such methods for synthesis include the Boc method, the Fmoc method, etc. The polypeptides of the invention can also be produced by the approaches of genetic engineerings.

Polypeptides Capable of Binding to Novel Receptors and/or G Proteins

As a result of the studies made by the present inventors, the polypeptides of the invention were found to have similar modes of action to fMLP for the following three reasons: (1) they are considered to exhibit neutrophil stimulating activity via a receptor that is expressed on the cells in the course of differentiation into neutrophil-like cells (see Example 6); (2) increase in the intracellular $Ca^{2+}$ concentration upon stimulation is likely to occur in response to the release of $Ca^{2+}$ from the intracellular $Ca^{2+}$ store and to the influx of $Ca^{2+}$ from outside of the cells (see Example 7); and (3) the polypeptides of interest are considered to activate neutrophils through activation of a receptor coupled conjugates with a PTX-sensitive G protein (see Example 8). However, among the various polypeptides of the invention, the one having SEQ ID NO:1 is considered to transmit information into cell either via a different receptor from that of fMLP (since the one having SEQ ID NO:1 does not inhibit the specific binding between [$^3$H]fMLP and fMLP receptor) or by directly activating the G protein (see Examples 9 and 10). Therefore, the present invention discloses the activation pathways which are different from what is mediated by fMLP and fMLP receptors. The receptors and their G protein which participate in these pathways can be obtained by the skilled artisan following the conventional methods used to obtain other receptors and G proteins.

The present invention further provides: (d) a polypeptide consisting of the amino acid sequence of SEQ ID NO:1; (e) a polypeptide consisting of an amino acid sequence derived from the amino acid sequence of SEQ ID NO:1 by deletion, substitution, insertion or addition of one or more amino acids and being capable of binding to a polypeptide (d)-binding receptor or G protein; or (f) a polypeptide consisting of an amino acid sequence biologically equivalent to the amino acid sequence of said polypeptide (d) or (e); (d) a polypeptide consisting of the amino acid sequence of SEQ ID NO:3; (e) a polypeptide consisting of an amino acid sequence derived from the amino acid sequence of SEQ ID NO:3 by deletion, substitution, insertion or addition of one or more amino acids and being capable of binding to a polypeptide (d)-binding receptor or G protein; or (f) a polypeptide consisting of an amino acid sequence biologically equivalent to the amino acid sequence of said polypeptide (d) or (e); (d) a polypeptide consisting of the amino acid sequence of SEQ ID NO:4; (e) a polypeptide consisting of an amino acid sequence derived from the amino acid sequence of SEQ ID NO:4 by deletion, substitution, insertion or addition of one or more amino acids and being capable of binding to a polypeptide (d)-binding receptor or G protein; or (f) a polypeptide consisting of an amino acid sequence biologically equivalent to the amino acid sequence of said polypeptide (d) or (e); and (d) a polypeptide consisting of the amino acid sequence of SEQ ID NO:5; (e) a polypeptide consisting of an amino acid sequence derived from the amino acid sequence of SEQ ID NO:5 by deletion, substitution, insertion or addition of one or more amino acids and being capable of binding to a polypeptide (d)-binding receptor or G protein; or (f) a polypeptide consisting of an amino acid sequence biologically equivalent to the amino acid sequence of said polypeptide (d) or (e).

When it is stated in this specification that a polypeptide is "capable of binding" to a certain polypeptide receptor or a certain G protein, the polypeptide except in special cases is capable of simple binding to (or may have "affinity" for) said polypeptide receptor (e.g. one of said novel receptors). Two cases are possible: one is that the result of binding causes the structural change in the receptor that permits to subsequently cause the polypeptide to exhibit various physiological actions and another is that the binding prevents other substances to bind to the receptor (in many cases, the polypeptide itself does not exhibit any physiological actions via the receptor). Whether a certain peptide can bind to the receptor or to the G protein according to the invention can be determined by the skilled artisan following the conventional methods used to measure the ability of a certain substance to bind to the other receptors and G proteins.

Peptides Associated with the Onset of Inflammations

As a result of their review, the present inventors found that, of the two neutrophil stimulating activities (one of causing neutrophils to migrate and the other of activating them), the polypeptides of the invention were likely to exhibit only the activity of causing neutrophils to migrate in a certain case (as at a certain concentration) and only the ability to activate neutrophils in another case (as at a concentration higher than the previously mentioned concentration) (Example 12). The inventors obtained the data supporting the possibility that the polypeptides of the invention would diffuse from a site of inflammation in the body to attract neutrophils (which are not activated at this stage) and that when neutrophils are attracted near to the site of inflammation, it causes increase in the concentration of the peptide of the invention relative to the neutrophils, and the neutrophils would stop migrating and be activated near the site of inflammation (see Example 12).

Therefore, the present invention provides: (a) a polypeptide consisting of the amino acid sequence of SEQ ID NO:1; (b) a polypeptide consisting of an amino acid sequence derived from the amino acid sequence of SEQ ID NO:1 by deletion, substitution, insertion or addition of one or more amino acids, said polypeptide having the activity of promoting the migration of neutrophils without promoting their activation or having the activity of promoting the activation of neutrophils without promoting their migration; or (c) a polypeptide consisting of an amino acid sequence biologically equivalent to the amino acid sequence of said polypeptide (a) or (b); (a) a polypeptide consisting of the amino acid sequence of SEQ ID NO:3; (b) a polypeptide consisting of an amino acid sequence derived from the amino acid sequence of SEQ ID NO:3 by deletion, substitution, insertion or addition of one or more amino acids, said polypeptide having the activity of promoting the migration of neutrophils without promoting their activation or having the activity of promoting the activation of neutrophils without promoting their migration; or (c) a polypeptide consisting of an amino acid sequence biologically equivalent to the amino acid sequence of said polypeptide (a) or (b); (a) a polypeptide consisting of the amino acid sequence of SEQ ID NO:4; (b) a polypeptide consisting of an amino acid sequence derived from the amino acid sequence of SEQ ID NO:4 by deletion, substitution, insertion or addition of one or more amino acids, said polypeptide having the activity of promoting the migration of neutrophils without promoting their activation or having the activity of promoting the activation of neutrophils without promoting their migration; or (c) a polypeptide consisting of an amino acid sequence biologically equivalent to the amino acid sequence of said polypeptide (a) or (b); and (a) a polypeptide consisting of the amino acid sequence of SEQ ID NO:5; (b) a polypeptide consisting of an amino acid sequence derived from the amino acid sequence of SEQ ID NO:5 by deletion, substitution, insertion or addition of one or more amino acids, said polypeptide having the activity of promoting the migration of neutrophils without promoting their activation or having the activity of promoting the activation of neutrophils without promoting their migration; or (c) a polypeptide consisting of an amino acid sequence biologically equivalent to the amino acid sequence of said polypeptide (a) or (b).

Methods of Treatment, Kits, Method of Screening, etc.

The polypeptides of the invention have neutrophil stimulating activity and hence are useful in diagnosing or treating diseases or conditions associated with the decrease or sub-normal functions of neutrophils (as exemplified by neutropenia). The polypeptides are also useful in unraveling methods for diagnosis or treatment of diseases or conditions associated with the activation of neutrophils including 'ischemic reperfusion injury' including cases resulting from 'myocardial infarction' and 'organ transplants', as well as 'type I diabetes' and inflammatory diseases including 'rheumatism', 'acute nephritis' and 'fulminant hepatitis'. Further, the polypeptides of the invention can be used to measure neutrophil stimulating activity, or can be used in a screening method to find substances useful in diagnostic testing or treatment of diseases or conditions associated with neutrophils, or in a process for producing substances useful in diagnostic testing or treatment of diseases or conditions associated with neutrophils, as well as in a kit for determining whether a substance will influence the neutrophil stimulating activity of the polypeptides of the invention, or in a kit for diagnostic testing or treatment of diseases or conditions associated with neutrophils.

Specifically, using substances useful in diagnostic testing or treatment of diseases or conditions associated with neutrophils, as exemplified by the polypeptides of the invention or antibodies against them, one may be able to achieve early detection, prevention, treatment, etc. of the above-mentioned cases of 'ischemic reperfusion injury', 'type I diabetes', as well as inflammatory diseases including 'rheumatism', 'acute nephritis' and 'fulminant hepatitis'.

In addition, by using substances that suppress the activities of the polypeptides of the invention such as antibodies that neutralize them to thereby suppress the infiltration of neutrophils, one may be able to treat the above-mentioned cases of 'ischemic reperfusion injury', 'type I diabetes', as well as inflammatory diseases including 'rheumatism', 'acute nephritis' and 'fulminant hepatitis'.

Further in addition, by administrating the polypeptides of the invention in excessive amounts to thereby prevent neutrophils from moving to a site of inflammation may be able to prevent inflammation in the above-mentioned cases of 'ischemic reperfusion injury', 'type I diabetes', as well as inflammatory diseases including 'rheumatism', 'acute nephritis' and 'fulminant hepatitis'.

The present invention provides: (1) a screening method for identifying a substance useful in diagnostic testing or treatment of a neutrophil-associated disease or condition, which includes the steps of (1) using a substance in combination with the polypeptide of the invention and (m) determining whether said substance will influence the neutrophil stimulating activity of said polypeptide; a process for producing a substance useful in diagnostic testing or treatment of a neutrophil-associated disease or condition, which includes the steps of (1) using a substance in combination with the polypeptide of the invention, (m) determining whether said substance will influence the neutrophil stimulating activity of said polypeptide, and (n) synthesizing said substance; as well as a kit for determining whether a substance will influence the neutrophil stimulating activity of the polypeptide of the invention which comprises (s) the polypeptide of the invention and/or the antibody to be described below and (t) a container for holding the polypeptide of the invention and/or the antibody mentioned below, or a kit comprising said antibody and container for diagnostic testing or treatment of a neutrophil-associated disease or condition. The expression "using a substance in combination with the polypeptide of the invention" as used herein covers, for example, contact between the substance and the polypeptide of the invention, as well as competitive use of the two. The expression "will influence the neutrophil stimulating activity of the polypeptide" covers promoting or inhibiting the neutrophil stimulating activity of the polypeptide of interest due, for example, to binding to or competing with said polypeptide.

The neutrophil stimulating activity of substances such as the polypeptides of the invention which are useful in diagnostic testing or treatment of neutrophil-associated diseases or conditions can be evaluated using neutrophils (including neutrophil-like cells). For example, a suspension of differentiated, neutrophil-like HL60 cells or human leukocyte cells is prepared and the polypeptide is added to stimulate the cells whereupon the cells or the neutrophils in the supernatant are activated; the neutrophil stimulating activity of the stimulant polypeptide can be evaluated by measuring the produced substance (i.e. activation markers such as β-HA). It is convenient to add cytochalasin B and DNase before stimulation and measuring the β-HA activity in the supernatant. Simultaneously measuring a marker substance for cell injury [e.g. lactate dehydrogenase (LDH) activity] is useful since this enables one to determine whether the polypeptide causes injury to the cells and also enables one to predict the mechanism behind the secretion of the activation markers (e.g. exocytosis). The polypeptides of the invention can also be evaluated by measuring the activity of promoting migration using undifferentiated HL60 cells or differentiated, neutrophil-like HL60 cells. The methods for measuring the activity of promoting migration are also well known to the skilled artisan. Any polypeptide that exhibits the activity of promoting neutrophil migration is included within the scope of the invention; however, the preferred polypeptides of the invention are those which exhibit the migration promoting activity for neutrophils but not for undifferentiated cells. For example, those which do not exhibit the migration promoting activity for undifferentiated HL60 cells but which exhibit the migration promoting activity for differentiated HL60 cells are preferred.

Antibodies

The present invention further provides antibodies against the polypeptides of the group described above. The antibodies are useful in diagnosis and treatment of diseases or conditions associated with the activation of neutrophils. Useful antibodies may be either monoclonal or polyclonal and monoclonal antibodies are more preferred. Monoclonal antibodies encompass those belonging to either one of immunoglobulin classes IgG, IgM, IgA, IgD and IgE and monoclonal antibodies of immunoglobulin classes IgG and IgM are advantageous. Methods well known to the skilled artisan may be employed to produce the antibodies. In order to produce a monoclonal antibody, the following procedure may be taken: the polypeptide of the invention is bound to a carrier protein and intraperitoneally injected, optionally with an adjuvant, into a mammal such as mouse, rat, guinea pig, hamster or rabbit, preferably mouse, in order to immunize them. Sensitization is repeated as many times as are required. When an appropriate antibody titer is obtained, antibody producing B cells are taken from the spleen, lymph node, bone marrow or tonsil, preferably the spleen, of the mammal and fused with myeloma cells, preferably those of the same species of origin as the mammal. By using a selective medium, hybrids between spleen cells, hybrids between myeloma cells, and unfused cells are removed. The obtained hybridomas are screened in view of their reactivity with the polypeptide of the invention and cells are obtained that produce a desired antibody to the polypeptide. The desired antibody can be obtained from the hybridomas by either the mouse ascites method or a method using a suitable medium and an incubator. Polypeptides prepared by modifying the polypeptides of the invention may be mentioned as substances that show the same actions as the antibodies of the invention.

When the polypeptides or antibodies of the invention are to be administrated for treatment, the route of administration is not limited in any particular way as long as the intended efficacy is exhibited and safe administration is realized. In addition, as long as the intended efficacy is exhibited and safe administration is realized, the dosage form is not limited in any particular way and may be determined as appropriate for the route of administration and the like. To formulate drug preparations, various pharmaceutically acceptable carriers may be added, as exemplified by antiseptics, moistening agents, emulsifiers, dispersing agents and stabilizers. A variety of drug preparations can be produced by the processes well known to the skilled artisan. The dose of administration can be determined as appropriate for various factors including the object of administration, the sex, body weight and age of the patient, dosage form, the symptoms of the disease to be treated, the route of administration, the frequency of administration and the time course of administration.

The antibodies of the invention can be evaluated on the basis of antigen-antibody reaction with the polypeptides of the invention by, for example, the well-known ELISA technique using the polypeptides of the invention as an antigen. Evaluation can also be made on the basis of the effectiveness in suppressing the neutrophil stimulating activity using said evaluation systems for neutrophil stimulation.

The following examples are provided for the purpose of further illustrating the present invention but are in no way to be taken as limiting the scope of the invention.

EXAMPLES

Examples 1-3 relate to the production of polypeptides. Examples 4 and 5 relate to the nucleophile stimulating activity of the polypeptides. Examples 6-10 relate to the mechanism by which the polypeptides activate neutrophils. Example 11 relates to the production of antibodies.

Example 1 (Purification of COSP-1 from Animal Tissue Material)

(1) Preparation of Crude Extracts

COSP-1 was prepared from normal porcine hearts. Immediately after slaughtering, porcine heart (about 2.2 kg each of 6) was extracted and bloodletting quickly using ice-cooled physiological saline (0.9% NaCl solution) following by washing and ice-cooling. Subsequently, the fat tissue and blood vessels in the surface layer of the heart were excised as much as possible under cooling with ice and the remainder was cut into thin slices about 5 mm thick; then, in order to minimize the proteolysis by the endogenous protease, the sliced tissue was heated in 16 L of ion-exchanged water at 100° C. for 10 minutes. The tissue was then cooled down to the room temperature and homogenized in 1 M acetic acid/20 mM HCl for 10 minutes using a whirling blender. To the homogenate, 1 M acetic acid containing 20 mM HCl was added to make a total volume of 10 L. Under stirring at 4° C. for 18 hours, extraction was performed to give a crude extract in solution. The extract in solution was centrifuged at 20,000 g for 10 minutes under cooling with ice and the supernatant was concentrated to 2.5 L. To the concentrated solution, ice-cooled acetone was added to give a final concentration of 60% and the mixture was stirred at 4° C. for 20 hours. Following a second centrifugation (20,000 g, 10 min, 4° C.), denatured protein were removed, and acetone was removed with an evaporator. Subsequently, degreasing and washing was performed twice or three times with diethyl ether. Thereafter, the liquid extract was concentrated to 1 L and further spun (20,000 g, 30 min, 4° C.) to remove the insoluble materials and the supernatant was concentrated under vacuum and freeze-dried to give a crude extract.

The crude extract, as evaporated to dryness, was dissolved in about 300 mL of 1 M acetic acid and subjected to a cation exchange chromatography on SP-Sephadex C-25 (7×37.5 cm, Pharmacia Biotech), whereupon it was separated into three fractions; fraction A as eluted with 1 M acetic acid, fraction P as eluted with 2 M pyridine, and fraction PA as eluted with 2 M pyridine-acetic acid (pH 5.0). The respective fractions were concentrated and freeze-dried. Among the three fractions, fraction PA was dissolved in 80 mL of 0.1 M acetic acid and separated by gel filtration chromatography on Sephadex G-25 column (4×146 cm, Pharmacia Biotech). For gel filtration chromatography, 0.1 M acetic acid was used as the mobile phase and 10 ml of each fraction eluted at a flow rate of 0.4 mL/min was collected using a fraction collector. For each of the fractions, the activity for β-HA secretion from differentiated HL60 cells was measured following the method described in Example 4. As a result, three different active fractions, PAG1 (eluted in an amount of 650-750 ml), PAG2 (eluted in an amount of 750-1100 ml) and PAG3 (eluted in an amount of 1450-1700 ml) were obtained. These procedures were repeated (for 6 hearts) to extract COSP-1 from porcine heart weighing 13.2 kg in total.

(2) Purification

Fraction PAG1 obtained in (1) was purified by reverse phase high-performance liquid chromatography (RP-HPLC) on a preparative ODS column (20×250 mm, Yamamura Kagaku). In the presence of 0.1% trifluoroacetic acid (TFA), a linear density gradient of acetonitrile was applied to elute fractions at a flow rate of 5 mL/min and the absorbance at 239 nm was monitored. A 15-mL aliquot was taken as each fraction and its activity for the secretion of β-HA from differentiated HL60 cells was measured. As a result, the activities were observed in two fractions, which were eluted at acetonitrile concentrations of 33-39% and 40-46%. They were designated PAG1-A and PAG1-B, respectively.

Subsequently, fraction PAG1-B was purified by high-performance liquid chromatography (HPLC) on a cation exchange column TSK-CM2SW (4.6×250 mm, Tosoh). In the presence of 10% acetonitrile, a linear density gradient of an ammonium formate buffer adjusted to pH 6.6 was applied to elute fractions at a flow rate of 1 mL/min and the absorbance at 280 nm was monitored. A 1-mL aliquot was taken for each fraction and its activity for the secretion of β-HA from differentiated HL60 cells was measured. As a result, the activity was observed in the fractions, which were eluted at an ammonium formate concentration of 88-109 mM (PAG1-BI) and 254-271 mM (PAG1-BII).

Further, fraction PAG1-BII was purified by RP-HPLC on an analytical C18 column (4.6×250 mm, 218TP54 Vydac). Fractions were eluted at a flow rate of 1 ml/min with a density gradient of acetonitrile being applied in the presence of 0.1% TFA and the absorbance at 280 nm was monitored. A 1-mL aliquot was taken for each fraction and, after being concentrated and evaporated to dryness with a concentrator, each fraction was dissolved in 200 μl of ultrapure water and the activity for β-HA secretion was measured. As a result, secretion activity, which was 71% of the value for the control, was observed in the 12th fraction eluted at an acetonitrile concentration of 33% [PAG1-BII (F12)]. Subsequently, this active fraction was further analyzed and purified by micro RP-HPLC on an analytical C2/C18 column (2.1×100 mm μ RPC C2/C18 SC2.1/10, Pharmacia Biotech) (flow rate, 100 μl/min). Since PAG1-BII (F12) contained impurities, the peak was taken [PAG1-BII (F12) peak], concentrated and evaporated to dryness. Thereafter, the peak was dissolved in 100 μl of ultrapure water and its activity was measured. As a result, secretion activity which was 84% of the value for the control, was observed as the single peak eluted at an acetonitrile concentration of 40%.

(3) Verification by Treatment with Thermolysin

In order to determine whether the active component in fraction PAG1-BII (F12) peak was a protein or polypeptide, enzymatic digestion by a proteolytic enzyme thermolysin was used for checking any effect it would have on the activity of the active substance. Specifically, the obtained fraction was mixed with thermolysin (1 mg/ml), which was dissolved in 0.1 M pyridine-HCl (pH 6.5) to make a 1:1 mixture of the sample and the thermolysin solution, and was kept at 45° C. for 24 hours for reaction. Then, to quench the enzymatic reaction, the mixture was reacted at 100° C. for 5 minutes. The β-HA secreting activity of the reacted solution was then measured.

As a result, the activity of the fraction in question completely disappeared upon digestion with thermolysin (12.8% of the value for the control before the treatment and 0.4% of the value for the control after the treatment). It was therefore shown that the component in a fraction PAG1-BII (F12) peak, which had β-HA secreting activity, was a protein or polypeptide.

(4) Structural Analyses a. Analysis of Amino Acid Sequences etc.

The molecular weight of the substance in fraction PAG1-BII (F12) peak was measured by fast atom bombardment mass spectrometry (FAB-MS) (JEOL JMS-HX/HX10A, JEOL). As a result, the substance in fraction PAG1-BII (F12) peak was found to have a molecular weight of 2568.2. Further, the spectra in mass spectrometry suggested that none of the substances in the fraction contained cysteine residues.

Further, fraction PAG1-BII (F12) peak was subjected to acid hydrolysis for analysis of the amino acid composition. The result is shown in the following table (Table 1).

TABLE 1

| Amino acid | PAG 1-BII (F12) peak (pmol) |
|---|---|
| Asx | 9.5 (2) |
| Glx | |
| Ser | 4.0 (1) |
| Gly | 4.3 (1) |
| His | 4.0 (1) |
| Arg | 7.7 (2) |
| Thr | 14.8 (4) |
| Ala | 9.4 (2) |
| Pro | 18.9 (5) |
| Tyr | |
| Val | 4.1 (1) |
| Met | 14.0 (3) |
| Ile | 21.0 (5) |
| Leu | 12.5 (3) |
| Phe | 4.2 (1) |
| Lys | 8.3 (2) |

Subsequently, the amino acid sequence was analyzed by the Edman method using an amino acid primary sequence analyzer (PPSQ-10, Shimadzu Corp.) The result is shown below.

SEQ ID NO:1, Leu-Ser-Phe-Leu-Ile-Pro-Ala-Gly-Trp-Val-Leu-Ser-His-Leu-Asp-His-Tyr-Lys-Arg-Ser-Ser-Ala-Ala

Thus, the substance in fraction PAG1-BII (F12) peak was a polypeptide consisting of 23 residues, none of which was a cysteine residue.

b. Analysis of C Terminus

In amino acid sequence analysis by the Edman method, it is impossible to determine whether the C terminus is an intact carboxyl group or a modified carboxyl group. Therefore, in order to clarify the C terminal structure of the polypeptide, it was analyzed by FAB-MS. As a result, the theoretical molecular weight calculated for the case where the C terminal was an intact carboxyl group agreed to the molecular weight determined by FAB-MS; hence, the C terminal of the polypeptide in question was found to be an intact carboxyl group.

c. Homology Search

In order to get information that would help in determining whether the obtained polypeptide was novel or not, a search for homology to the known sequences was conducted using a database Genome Net WWW (Location; http://www-.genome.ad.jp/). As a result, the polypeptide of interest was 82% homologous to the 23 residues at the C terminus of bovine heart cytochrome C oxidase subunit VIII (19 out of the 23 residues were identical) and this polypeptide was predicted to be a bovine heart cytochrome C oxidase subunit VIII related peptide. The polypeptide was therefore named cytochrome C oxidase subunit peptide-1 (COSP-1). Listed below are the 23 residues at the C terminus of bovine heart cytochrome C oxidase subunit VIII.

SEQ ID NO:2, Leu-Ser-Phe-Leu-Leu-Pro-Ala-Gly-Trp-Val-Leu-Tyr-His-Leu-Asp-Asn-Tyr-Lys-Lys-Ser-Ser-Ala-Ala

COSP-1 was 57% homologous to the C terminal portion of human cytochrome C oxidase subunit VIII (12 out of the 21 residues were identical). The sequence is shown below.

SEQ ID NO:3, Val-Thr-Phe-Leu-Leu-Pro-Ala-Gly-Trp-Ile-Leu-Ser-His-Leu-Glu-Thr-Tyr-Arg-Arg-Pro-Glu

Example 2 (Purification of fCyt b (1-15) from Tissue Animal Materials)

(1) Purification

The PAG1 obtained in Example 1 was first purified by RP-HPLC on a preparative ODS column (20×250 mm, Yamamura Kagaku) and each of the fractions obtained was concentrated and evaporated to dryness with a concentrator and thereafter dissolved in ultrapure water for measurement of secretion activity. To perform RP-HPLC, a linear density gradient of acetonitrile was applied in the presence of 0.1% trifluoroacetic acid (TFA) and fractions were eluted at a flow rate of 5 ml/min; after monitoring the absorbance at 230 nm, a 15-mL aliquot was taken for each fraction. As a result, the most active fraction was eluted at an acetonitrile concentration of about 27-31% and was designated as PAG1-I. The fraction PAG1-I was purified by cation-exchange HPLC on a TSK-CM2SW column (4.6×250 mm, Tosoh) and its activity was measured. To perform cation-exchange HPLC, a linear density gradient of an ammonium formate buffer adjusted to pH 6.6 was applied in the presence of 10% acetonitrile and fractions were eluted at a flow rate of 1 ml/min; after detecting the absorbance at 280 nm, a 1-mL aliquot was taken as each fraction. As a result, secretion activity was observed in the following three fractions: the fraction eluted at an ammonium formate concentration of 156-165 mM (PAG1-I-a), of 214-228 mM (PAG1-I-b), and of 234-241 mM (PAG1-I-c).

Among these fractions, PAG1-I-c was further purified by micro RP-HPLC on an analytical C4 column (Develosil C4, 1.0×150 mm, Nomura Kagaku), with a density gradient of acetonitrile applied in the presence of 0.1% TFA to elute fractions at a flow rate of 50 μl/min. Activity was observed in the following three fractions: the fraction eluted at an acetonitrile concentration of 24% (PAG1-I-c1), of 26% (PAG1-I-c2), and of 27% (PAG1-I-c3). The most active fraction PAG1-I-c2 was further purified by micro RP-HPLC on an analytical C18 column (Develosil C18, 1.0×250 mm, Nomura Kagaku) with a density gradient of acetonitrile applied in the presence of 0.1% TFA to elute fractions at a flow rate of 50 μl/min; activity was observed in the peak eluted at an acetonitrile concentration of 26%. The purity of this active fraction was assayed and further purification was performed by eluting from the same analytical C18 column; a single elution peak was obtained that agreed to the activity.

(2) Structural Analysis

In order to know the structure of the substance in the fraction, molecular weight measurement was conducted with TOF-MS (Voyger Elite, Perseptive). As a result, the substance in the fraction PAG1-I-c2 was found to have a molecular weight of 1806.47. Mass spectrometry by FAB-MS showed that the substance had a mass of 1805.1.

In order to obtain the structural information about this active substance FAB-MS/MS or tandem mass spectrometry using FAB was performed. The following sequence information was obtained, with the parenthesized numerals indicating the amounts of residues (their molecular weights).

N terminal side: (260)-(227)-Arg-Lys/Gln-Ser-His-Pro-Leu-: C terminal side

The active fraction was treated with Arg-C, an enzyme capable of cleaving the C terminal side of the residue Arg. To be specific, 20 μl of a 50 mM sodium phosphate buffer containing 4 pmol of Arg-C was added to the concentrated and dried purified substance and the mixture was incubated at 37° C. for 16 hours. The incubated mixture was purified by micro RP-HPLC on a Develosil C18 column (1.0×250 mm, Nomura Kagaku). In micro RP-HPLC, a density gradient of acetonitrile was applied in the presence of 0.1% TFA to elute fractions at a flow rate of 50 μl/min; four fractions showing an absorbance peak at 214 nm were monitored and designated A, B, C and D in the order of the eluting speed. These fractions were subjected to the primary structural analysis of amino acids. The result is shown in the following table (Table 2).

TABLE 2

| | Amino acid sequence |
|---|---|
| A | Lys-Ser-His-Pro-Leu-Met-Lys (SEQ ID NO: 6) |
| B | — |
| C | Lys-Ser-His-Pro-Leu-Met-Lys-Ile-Ile-Asn (SEQ ID NO: 7) |
| D | X-Asn-Ile-Arg- |

X: Not detected

A homology search on the sequence of C showed that it had the same sequence as swine cytochrome b (6-15) which was a mitochondria protein. Further, the values of 260 and 227 indicating the amounts of the residues from the N terminus of the active fraction as determined by FAB-MS/MS agreed to the values for the amounts of the residues fMet-Thr and Asn-Ile in swine cytochrome b (1-4).

Thus, on the basis of the sequence of the partial polypeptide obtained by treatment with Arg-C and from the structural information obtained by FAB-MS/MS, the substance in the active fraction of interest was predicted to be identical to swine cytochrome b (1-15) and have the following sequence.

SEQ ID NO:4, fMet-Thr-Asn-Ile-Arg-Lys-Ser-His-Pro-Leu-Met-Lys-Ile-Ile-Asn

The molecular weight as calculated from the sequence (fCyt b (1-15)) obtained by homology search was 1824.19 and not the same as 1805.1 which was the value obtained by FAB-MS; however, FAB-MS/MS suggested the possibility that the C terminal portion of the substance in the active fraction may have been modified.

Further, the sequence as determined for swine b (1-15) was 67% homologous to human cytochrome b (1-15) (10 out of the 15 residues were identical). The sequence is shown below.

SEQ ID NO:5, fMet-Thr-Pro-Met-Arg-Lys-Ile-Asn-Pro-Leu-Met-Lys-Leu-Ile-Asn

Example 3 [Synthesis of COSP-1 and fCyt b (1-15) (Swine and Human)]

Synthesis of polypeptides was performed by the Boc method or the Fmoc method following the Merrifield's solid-phase method in a simplified glass reaction vessel.

(1) Materials $N^\alpha$-t-butoxycarbonyl(Boc)-L-Ala-phenylacetamidomethyl (PAM) resin and hydroxymethylphenoxy (HMP) resin were purchased from Watanabe Kagaku Kogyo, and N,N'-dicyclohexylcarbodiimide (DCC), 1-hydroxybenzotriazole (HOBt), Boc-amino acid and 9-fluorenylmethyloxycarbonyl (Fmoc)-amino acid were purchased from Peptide Institute Inc. The other common reagents were available from Wako Pure Chemical Industries, Ltd.

(2) Synthesis by the Boc Method

In polypeptide synthesis by the Boc method, a PAM resin was used as a solid-phase carrier and a Boc group was used to protect the α-amino group in amino acids. As protective groups for the side chains on Boc-amino acids, a cyclohexyl group was used for Asp, a benzyl group for Ser and Tyr, a 2,4-dinitrophenyl (Dnp) group for His, and a tosyl group for Arg.

In the first step, a Boc-X-PAM resin (X is the C terminal amino acid in the polypeptide to be synthesized) was treated with 50% TFA to cleave the Boc group at the N terminal; in the next step, a Boc-amino acid in 2.5 equivalents relative to the amount of Boc-X to be introduced was condensed by the DCC-HOBt method. A few hours later, a Kaisar ninhydrin test was conducted to check for the completion of the reaction and if the reaction was found to be incomplete, a second condensation reaction was run. In this way, the cleavage of the Boc group and the condensation reaction for the protected amino acid were repeated so that the polypeptide chain would extend progressively from the C terminus to produce a protected polypeptide resin. In order to protect the indole ring of Trp, 50% TFA containing 2% ethane dithiol was used to cleave the Boc group after introducing the Trp residue.

Deprotection of the protected polypeptide resin and release of the polypeptide from the resin were done by treatment with anhydrous hydrogen fluoride. In the presence of 0.5 ml of anisole as well as 1 ml each of thioanisole, ethane dithiol and methyl sulfide per gram of the protected polypeptide resin, the resin was treated for 1 hour with 10 ml of anhydrous hydrogen fluoride under cooling with ice so that the polypeptide was released from the resin and the protecting groups were removed at the same time. Immediately after the reaction, HF was removed under vacuum and the polypeptide/resin mixture was washed with diethyl ether. Then, the polypeptide was extracted with 60% acetonitrile, concentrated under vacuum and freeze-dried to give a crude polypeptide. In the case where His was contained in the protected polypeptide resin, the Dnp group was removed by the reaction with thiophenol (20 mmol/mmol Dnp group) for 1 hour. Then, the Boc group at the N terminus was cleaved and treatment with anhydrous hydrogen fluoride was performed.

(3) Synthesis by the Fmoc Method

In polypeptide synthesis by the Fmoc method, an HMP resin was used as a solid-phase carrier and an Fmoc group was used to protect an α-amino group. To protect side chains, a triphenylmethyl (Trt) group was used for Asn and His, a tert-butyl (t-Bu) group for Ser and Tyr, a 4-methoxy-2,3,6-trimethylbenzenesulfonyl (Mtr) group for Arg, and a tert-butoxycarbonyl (Boc) group for Lys.

In the first step, the HMP resin was swollen in dichloromethane (DCM) and reacted with 2 equivalents of DCC, 0.2 equivalents of dimethylaminopyridine (DMAP) and 2 equivalents of Fmoc-Asn (Trt) in N,N'-dimethylformamide (DMF) for 1 hour to give an Fmoc-Asn (Trt)-HMP resin. To determine the amount of an amino acid introduced into the HMP resin, the amount of N-(9-fluorenylmethyl)piperidine generated by treatment with piperidine: DMF (3:7) was quantitated by measuring the absorbance at 301 nm. To extend the polypeptide chain, the Fmoc-amino acid-resin was treated in 20% piperidine-N-methylpyrrolidone (NMP) for about 30 minutes to remove the Fmoc group and, thereafter, Fmoc-amino acid, HOBt and DCC were added at 5 equivalents and N,N',N"-diisopropylethylamine (DIEA) added at 1 equivalent relative to the introduced C-terminal amino acid and condensation was performed for 30 minutes to several hours, and these procedures were performed repeatedly. Elimination of the Fmoc group and the progress of the condensation reaction were checked by a ninhydrin test for a small amount of the resin taken out from the reaction mixture.

In order to introduce a formyl group at the N terminus, the Fmoc group was removed from the polypeptide resin that had completed the extension of the polypeptide chain and the polypeptide resin was reacted with 20 equivalents of formic acid, DCC and HOBt in DMF. The end of the reaction was stopped by monitoring by a ninhydrin test. Deprotection of the protected polypeptide resin and release of the polypeptide from the resin were done by treatment for 3 hours with a TFA solution containing phenol and thioanisole as scavengers (TFA:phenol:thioanisole:water=82.5:5:5:5). After the end of the reaction, the reaction mixture was concentrated and removed and the polypeptide was extracted with 1-M acetic acid and the resin was separated by filtration. Thereafter, the extracted polypeptide was washed three times with diethyl ether to remove the scavengers, concentrated under vacuum and freeze-dried to give a crude polypeptide.

(4) Purification of the Synthesized Polypeptide

The synthesized polypeptide was purified by RP-HPLC on a TSK gel ODS-80Ts (20×250 mm, Tosoh) column. A linear density gradient of acetonitrile was applied in the presence of 0.1% TFA to elute fractions at a flow rate of 5 ml/min; a main peak was taken by referring the absorbance at 214 nm and freeze-dried to give a purified polypeptide. Its purity was verified by analytical RP-HPLC on a Beckman ODS (4.5×250 mm) column. Specifically, as in the case of purifying the polypeptide, a linear density gradient of acetonitrile was applied in the presence of 0.1% TFA to elute fractions at a flow rate of 1 ml/min and verification was made by reference to the absorbance at 214 nm. The purified polypeptide was hydrolyzed in 6 N HCl containing 2% phenol and 2% thioglycolic acid at 110° C. for 24 hours and the hydrolyzate was analyzed with an amino acid analyzer to check the amino acid composition of the polypeptide and the contents of the respective amino acids.

Example 4 (β-HA Secreting Activity)

The synthesized COSP-1, fCyt b (1-15) and Cyt b (1-15) (porcine and human) were checked for their β-HA secreting activity.

(1) Materials

HL60 cells derived from human promyelocytic leukemia cells were purchased from Riken Cell Bank. Fetal calf serum (FCS) was purchased from Biotech International, RPMI-1640 medium from GIBCO BRL, bovine serum albumin (fraction V, fatty acid-free) (BSA) from Calbiochem-Novabiochem, as well as N6,2'-O-dibutyryladenosine 3':5'-cyclic monophosphate (db-cAMP), cytochalasin B, deoxyribonuclease I (DNase I), fMLP and p-nitrophenyl N-acetyl-β-D-glucosaminide from SIGMA, β-nicotinamide adenine dinucleotide (NAD) from Tokyo Chemical Industries, Ltd., and streptomycin sulfate and crystalline penicillin G from Meiji Seika, Ltd.

(2) Method a. Cultivation of HL60 Cells and Induction to the Differentiated Neutrophil-Like Cells For cultivation, heat-inactivated FCS (final concentration; 10%), streptomycin (final concentration; 100 mg/l), penicillin G (final concentration of $10^5$ units/l) and RPMI-1640 culture solution containing 10 mM Hepes (pH 7.4) were used. Cells were cultivated at a cell density of $2 \times 10^5$-$1.5 \times 10^6$ cells/ml in a plastic flask (80 cm$^2$, 260 ml, Nunc) at 37° C. under stationary conditions with a 5% of $CO_2$ concentration and a 100% of humidity.

In order to differentiate the HL60 cells into neutrophil-like cells, db-cAMP as a differentiation inducer was added at a final concentration of 0.5 mM, when the cell density in the flask had reached $1.0 \times 10^6$ cells/ml, then the cells were further cultured for 3 days.

b. Preparation of Human Leukocytes

Thirty milliliters of human peripheral blood (containing 500 units of heparin sodium) was plated on 5 ml of Lymphocepal I in each of 4 centrifugal tubes and spun down (400 g, 30 min) at room temperature. After spinning, the monocytes and lymphocytes forming a turbid layer at the interface between the plasma and Lymphocepal I were carefully taken to be removed. In the next step, the layer of erythrocyte cells containing neutrophils was washed with phosphate buffered saline (PBS; 139 mM NaCl, 8.18 mM $Na_2HPO_4$, 1.82 mM $NaH_2PO_4$, pH 7.4) and plated on 85% Percoll-Hepes equilibrated Hank's buffer (10 mM Hepes, 136.9 mM NaCl, 5.4 mM KCl, 1.2 mM $CaCl_2$, 0.44 mM $KH_2PO_4$, 0.49 mM $MgCl_2$, 0.41 mM $MgSO_4$, 0.34 mM $Na_2HPO_4$, 4.2 mM $NaHCO_3$, pH 7.4) and spun down (800 g, 10 min) to precipitate the erythrocyte cells. The Percoll layer containing neutrophils was carefully taken and washed with physiological saline. Then, it was replaced by a 0.2% NaCl solution and about 30 seconds later, an equal amount of 1.6% NaCl aqueous solution was added; this procedure was repeated twice, whereby the left erythrocytes were lysed and neutrophils were isolated.

The purities of these monocyte-lymphocyte mixed cells and neutrophils were assayed by analysis with a flow cytometer. Propidium iodide was added to the cell suspension at a final concentration of 100 ng/ml in order to stain dead cells. Using a flow cytometer, forward scatter intensity and side scatter intensity were measured on a linear scale only for the negative cells (living cells) in the cell suspension for the propidium iodide-staining. The results were processed by CellQuest software and represented as a dot plot of forward scatter intensity (X-axis) and side scatter intensity (Y-axis). The purify of monocycle-lymphocyte mixed cells were 84% and that of the neutrophils were 83%.

c. Stimulation of the Cell

The differentiated HL60 cells and human leukocyte cells were washed three times with ice-cooled 0.1% BSA containing Hepes buffered Hank's solution (HBHS; 10 mM Hepes, 136.9 mM NaCl, 5.4 mM KCl, 1.2 mM $CaCl_2$, 0.44 mM $KH_2PO_4$, 0.49 mM $MgCl_2$, 0.41 mM $MgSO_4$, 0.34 mM $Na_2HPO_4$, 5.5 mM glucose, 4.2 mM $NaHCO_3$, pH 7.4). A cell suspension was prepared for each cell type at $5.5 \times 10^6$ cells/ml. Cytochalasin B and DNase I were then added to each cell suspension at a final concentration of 5 μg/ml. Ninety μl of each cell suspension was then transferred to an ice-cooled tube ($5.0 \times 10^5$ cells/tube) and incubated at 37° C. for 10 minute. To each tube, either one of the fractions of polypeptide (or extract) in solution (10 μl) was added and incubated at 37° C. for 10 minutes to stimulate the cells. Immediately after the treatment, 200 μl of ice-cooled reaction quenching buffer (25 mM Tris, 123 mM NaCl, 2.7 mM KCl, pH 7.4) was added to the cell suspensions to stop the stimulation. Thereafter, the tubes were spun down at 4° C. for 60 seconds to precipitate the cell pellets and the β-HA activity and the lactate dehydrogenase (LDH) activity in the supernatant were measured.

d. Measuring β-HA Enzyme Activity

The amount of β-HA secreted into the reaction supernatant was determined by measuring the absorbance at 415 nm of p-nitrophenol that was generated by an enzymatic reaction involving p-nitrophenyl N-acetyl-β-D-glucosaminide as a substrate. To be specific, 90 μl of the reaction supernatant was transferred to a 96-well Immuno plate (Nunc) and 60 μl of a substrate solution (10 mM p-nitrophenyl N-acetyl-β-D-glucosaminide/40 mM citrate, 70 mM $Na_2HPO_4$, pH 4.5) was added to initiate an enzymatic reaction. Following a 1-hr reaction at 37° C., 100 μl of a reaction quencher (400 mM glycine, pH 10.7) was added to stop the reaction and the absorbance at 415 nm was measured. As a control, cells were treated with Triton X-100 at a final concentration of 0.05% and the amount of β-HA in the supernatant was measured. As another control, the amount of β-HA secreted from cells upon stimulation with fMLP at a final concentration of 10 μM was measured.

The β-HA enzyme activity secreted in the reaction mixture was expressed either as the percentage of the total enzyme activity in cells (%/total) which was the enzyme activity of β-HA released upon distraction of the cells with 0.05% Triton X-100, or as the percentage of maximum secretion activity (%/control) which was the enzyme activity of β-HA released upon stimulation with 10 μM of fMLP.

e. Measuring LDH Enzyme Activity

The amount of LDH secreted into the reaction mixture was determined by measuring the absorbance (340 nm) of NADH generated by reduction of that NAD involves dehydrogenation of lactate. Reaction was initiated by adding a 400 μl of a substrate-buffer solution (125 mM 2-amino-2-methyl-1-propanol, 125 mM lithium lactate, 6.25 mM NAD, pH 9.5) to a 100 μl of the reaction supernatant. Following a 1-hr incubation at 37° C., the mixture was quenched in ice water to stop the reaction and the absorbance at 340 nm was measured.

The LDH enzyme activity secreted in the reaction mixture was expressed as the percentage of the total enzyme activity in cells (%/total) which was the enzyme activity of LDH released upon disruption of the cells with 0.05% Triton X-100.

(2) Results and Discussion a. β-HA Secretion Activity for the Differentiated HL60 Cells The results are shown in the following tables (Tables 3 and 4) and FIG. 1.

TABLE 3

|  | $EC_{50}$ (nM) | Percentage of maximum secretion activity (%/control) |
|---|---|---|
| fMLP | 5.3 ± 0.8 | 100 |
| COSP-1 | 270 ± 20 | 93.6 ± 2.8 |
| fCyt b (1-15) | 38.0 ± 3.4 | 113.0 ± 2.3 |
| Cyt b (1-15) | >6 × 10³ | >31 |

TABLE 4

|  | β-HA secretion from differentiated HL60 cells (%/total) |
|---|---|
| Not stimulated | 2.8 |
| fMLP | 67.4 |
| fCyt b (1-15) | 76.2 |
| Human fCyt b (1-15) | 65.9 |
| COSP-1 | 63.1 |
| Human COSP-1 | 53.5 |

Both COSP-1 and fCyt b (1-15) stimulated β-HA secretion from differentiated HL60 cells in a dose dependent manner ($EC_{50}$: COSP-1 $2.67 \times 10^{-7}$ M, fCyt b (1-15) $3.80 \times 10^{-8}$ M). It was also shown that Cyt b (1-15) had stimulating activity, although it was about less than 1/1000 of the value for fCyt b (1-15). However, no LDH was found to leak out of the cells when they were stimulated with those polypeptides. Therefore, COSP-1, fCyt b (1-15) and Cyt b (1-15) were found to promote the secretion of β-HA by inducing exocytosis of the differentiated HL60 cells.

In addition, human COSP-1 and human fCyt b (1-15) which were the human homologues of COSP-1 and fCyt b (1-15), were shown to be comparable to COSP-1 and fCyt b (1-15) in the activity for β-HA secretion from the differentiated HL60 cells.

b. β-HA Secreting Activity for Human Neutrophils

The results are shown in the following table (Table 5).

TABLE 5

|  | β-HA secretion from neutrophil cells (%/total) | β-HA secretion from monocyte and lymphocyte mixed cells (%/total) |
|---|---|---|
| Not stimulated | 17.9 | 16.3 ± 5.0 |
| COSP-1 | 40.5 | — |
| fMLP | 68.3 | 21.8 ± 5.3 |
| fCyt b (1-15) | 58.3 | 20.0 ± 7.8 |

The secretion of β-HA from human neutrophils was 17.9% in the absence of stimuli, whereas it was 68.3% upon stimulation with 10 μM fMLP, 40.5% upon stimulation with 10 μM COSP-1 and 58.3% upon stimulation with 10 μM fCyt b (1-15). The secretion of β-HA was obviously increased by stimulation with these polypeptides. In the monocyte and lymphocyte mixed cells, the secretion of β-HA was 16.3±6.0% in the absence of stimuli, whereas it was 21.8±5.3% upon stimulation with 10 μM fMLP and 20.0±7.8% upon stimulation with 10 μM fCyt b (1-15). Thus, β-HA secreting activity was clearly positive upon stimulation with those polypeptides, although the level was slight. However, as no LDH was found to leak out from either the neutrophil cells or the monocyte and lymphocyte mixed cells, these polypeptides were found to promote the secretion of P-HA by causing exocytosis without damaging the human neutrophils.

Example 5 (Migration Promoting Activity)

Neutrophil activating factors, such as fMLP and interleukin 8, are known to have migration promoting activity and secretion promoting activity of β-HA and various other degradative enzymes from neutrophils. In this section migration promoting activity of COSP-1 and fCyt b (1-15) were evaluated for the undifferentiated HL60 cells or neutrophil-like differentiated HL60 cells.

(1) Method

The migration promoting activity of each of the polypeptides of interest was measured using Chemotaxis Cells (Kurabo) as follows: The differentiated HL60 cells or undifferentiated HL60 cells were washed three times with ice-cooled HBHS and a cell suspension was prepared at a cell density of $4 \times 10^6$ cells/ml. The cell suspension was incubated at 37° C. for 10 minutes; thereafter, 500 μl of the cell suspension was transferred to Chemotaxis Cells ($2 \times 10^6$ cells/Cell), which were put on a micro-well plate filled with pre-heated (37° C.) HBHS containing 1 ml of polypeptide and incubation was performed at 37° C. for 1 hour. Then, the Chemotaxis Cells were removed from the plate and the number of cells that had migrated in each well was counted.

Migration promoting activity was expressed by a chemotaxis index, or the number of cells that migrated upon stimulation was divided by the number of cells migrated without stimuli.

(2) Results and Discussion

Figure 2:
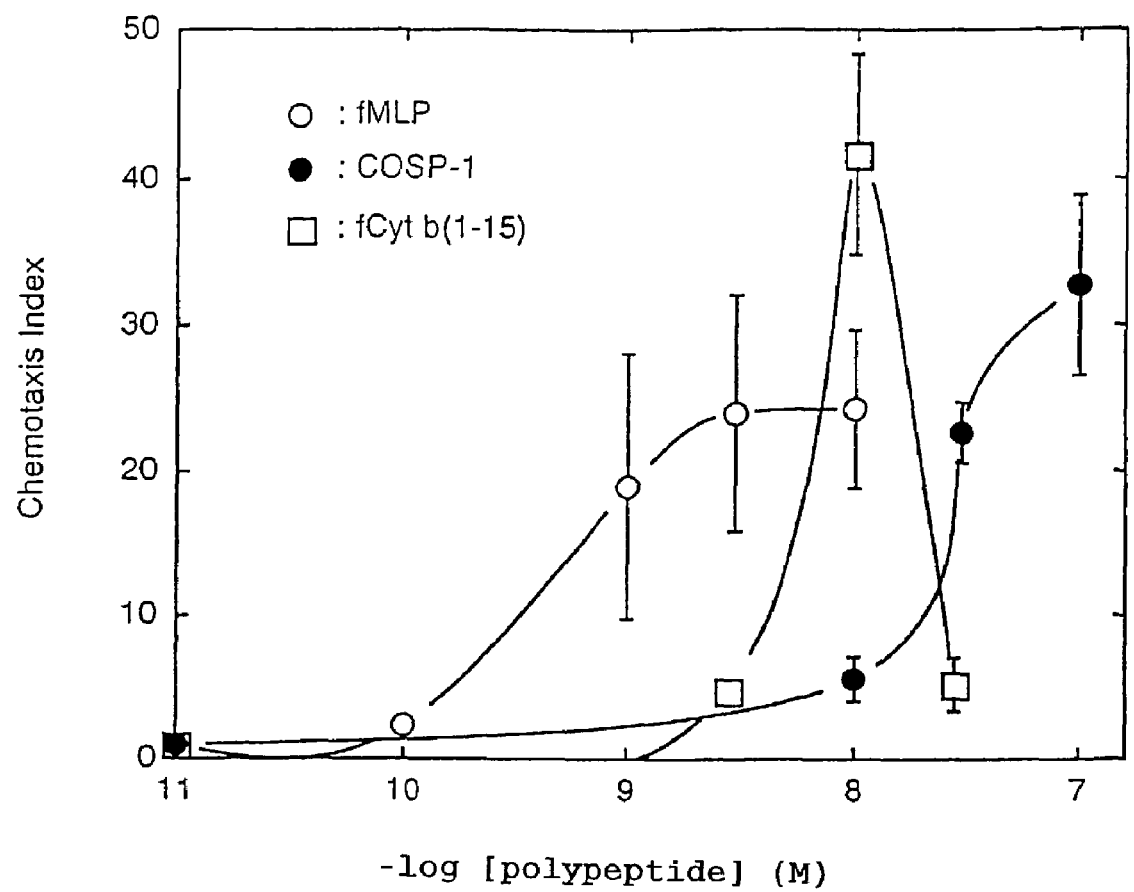
FIG. 2 shows the results of experiments on the activity of polypeptides in inducing migration of the HL60 cells that differentiated into neutrophil-like cells (Example 5) [○, fMLP; ●, COSP-1; □, fCyt b (1-15)]

The results are shown in FIG. 2.

The polypeptides under test did not show migration promoting activity in the undifferentiated HL60 cells but they showed attracting activity in a dose dependent manner in the differentiated HL60 cells.

Example 6 (Effect of Differentiation on the Secreting Activity of the HL60 Cells)

When HL60 cells are treated with db-cAMP, fMLP receptors are expressed on the surfaces of the cells as they differentiate into neutrophil-like cells. The amount of the fMLP receptors is increased in a time-dependent manner. The investigation was made in order to know how the secretion of β-HA by COSP-1 would varies with the difference in the differentiation stage of the HL60 cells.

(1) Method

Cells were cultivated following the method as described in Example 4, except that the RPMI-1640 medium containing contained 15% of FCS, and that in order to differentiate the HL60 cells into neutrophil-like cells, a cell suspension was prepared such that the cell density in the flask would be $0.5 \times 10^6$ cells/ml at the time of addition of db-cAMP (final concentration, 0.5 mM). The β-HA secretion promoting activities of COSP-1 and fMLP were measured 24, 48 and 72 hours after the differentiation.

(2) Results and Discussion

Figure 3:
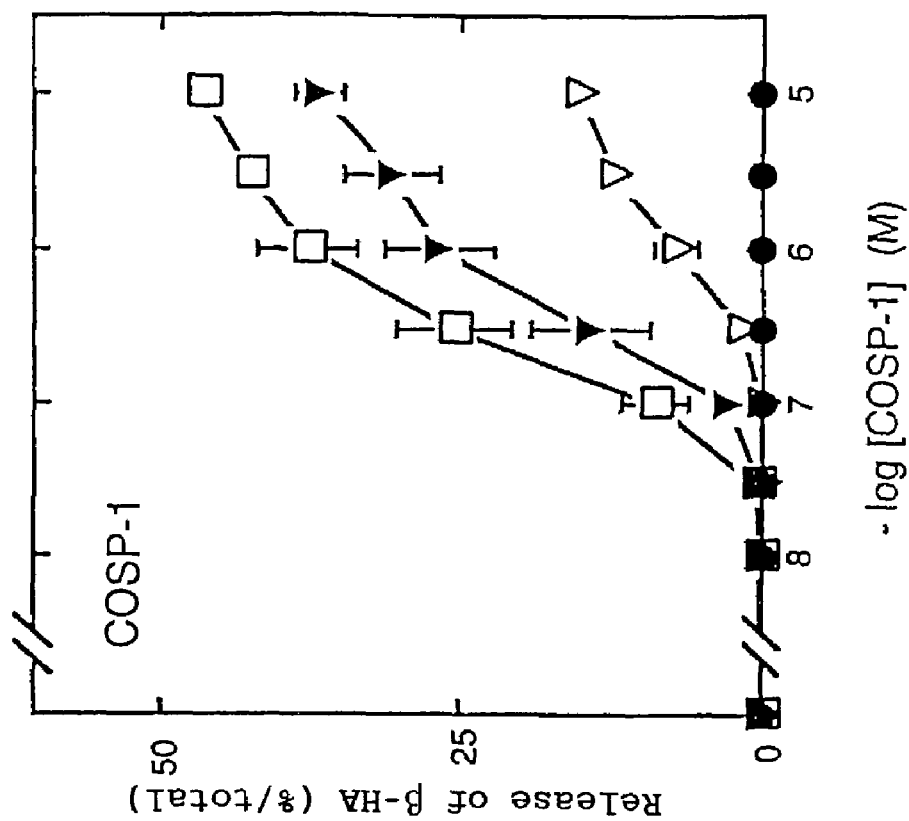
FIG. 3 shows the results of experiments on the effect of the polypeptides on differentiation of the HL60 cells (Example 6) [●, undifferentiated, ∇, 24 hours after differentiation; ▼, 48 hours after differentiation; □, 72 hours after differentiation)]
Figure 3:
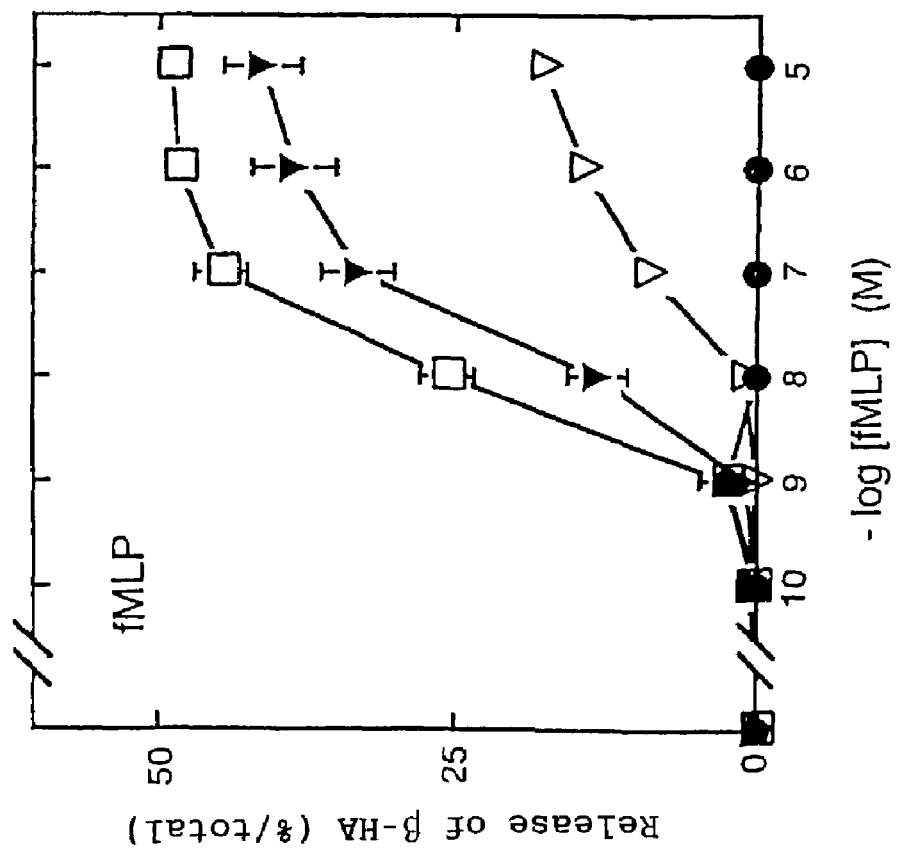

The results are shown in the following table (Table 6) and FIG. 3.

TABLE 6

|  |  | Differentiation | | |
|---|---|---|---|---|
|  |  | 0 hr | 24 hr | 48 hr | 72 hr |
| COSP-1 | $EC_{50}$ (M) | — | $1.2 \times 10^{-6}$ | $4.5 \times 10^{-7}$ | $2.7 \times 10^{-7}$ |
|  | Max. (%/total) | — | 15.6 | 35.7 | 45.3 |
| fMLP | $EC_{50}$ (M) | — | $1.1 \times 10^{-7}$ | $2.2 \times 10^{-8}$ | $9.3 \times 10^{-9}$ |
|  | Max. (%/total) | — | 17.4 | 40.6 | 48.4 |

—: No activity
Max.: Maximum secretion on average

Neither COSP-1 nor fMLP caused the β-HA secretion to the undifferentiated HL60 cells. However, after the differentiation, they caused secretion in a dose-dependent manner at the respective times of measurement. As the differentiation progressed, the maximum secretion of β-HA was increased and so did its sensitivity. In addition, neither of COSP-1 and fMLP caused LDH leakage from the HL60 cells. Therefore, it was suggested that COSP-1 and fMLP would promote the secretion of β-HA through the receptor whose expression was accompanied following the differentiation stage of HL60 cells.

Example 7 (Effect on Intracellular $Ca^{2+}$ Concentration)

Furthermore, the investigation was made in order to know how such stimulation by COSP-1 would affect the intracellular $Ca^{2+}$ concentration ($[Ca^{2+}]i$) of the HL60 cells. The data were compared with the results previously reported for the stimulation by fMLP.

(1) Method

The differentiated HL60 cells or undifferentiated HL60 cells were washed twice with a Hepes-Na solution (140 mM NaCl, 4 mM KCl, 1 mM $NaH_2PO_4$, 1 mM $MgCl_2$, 1.25 mM $CaCl_2$, 5 mM Hepes, 11 mM glucose, 0.2% BSA, pH 7.4). Then, $Ca^{2+}$ sensitive fluorescence reagent, fura-2/AM, was added to the cell suspension (4 ml: final concentration, 4 μM). The reaction mixture was then shaken gently at room temperature for 60 minutes, shielded from light in order to incorporate fura-2 into the HL60 cells. Subsequently, the cells were washed twice with a Hepes-Na solution and a cell suspension was prepared at a final cell density of $1.0 \times 10^6$ cells/ml. One milliliter of the cell suspension was put into reaction cuvettes and stimulated with various samples under stirring at 30° C. Ratios of fluorescence intensity at 500 nm (F) for an excitation wavelength at 340 nm to that at 380 nm were measured with a fluorimeter (CAF-100, Japan Spectroscopic Co., Ltd.) and $[Ca^{2+}]i$ was calculated following the formula:

$$[Ca^{2+}]i(nM) = K \times \{(F-Fmin)/(Fmax-F)\} \times A/B,$$

wherein

Fmax: a ratio of fluorescence intensity at 500 nm for an excitation wavelength at 340 nm to that at 380 nm after all cells were solubilized with 0.1% Triton X-100;

Fmin: a ratio of fluorescence intensity at 500-nm for an excitation wavelength at 340 nm to that at 380 nm after the whole calcium was chelated with 4 mM EGTA;

A: fluorescence intensity at 500-nm for an excitation wavelength at 380 nm, when all the calcium was chelated with EGTA;

B: fluorescence intensity at 500-nm for an excitation wavelength at 380 nm, when all cells were solubilized with Triton X-100;

K: 224 (nM) (the dissociation constant of fura-2).

(2) Results and Discussion

Figure 4:
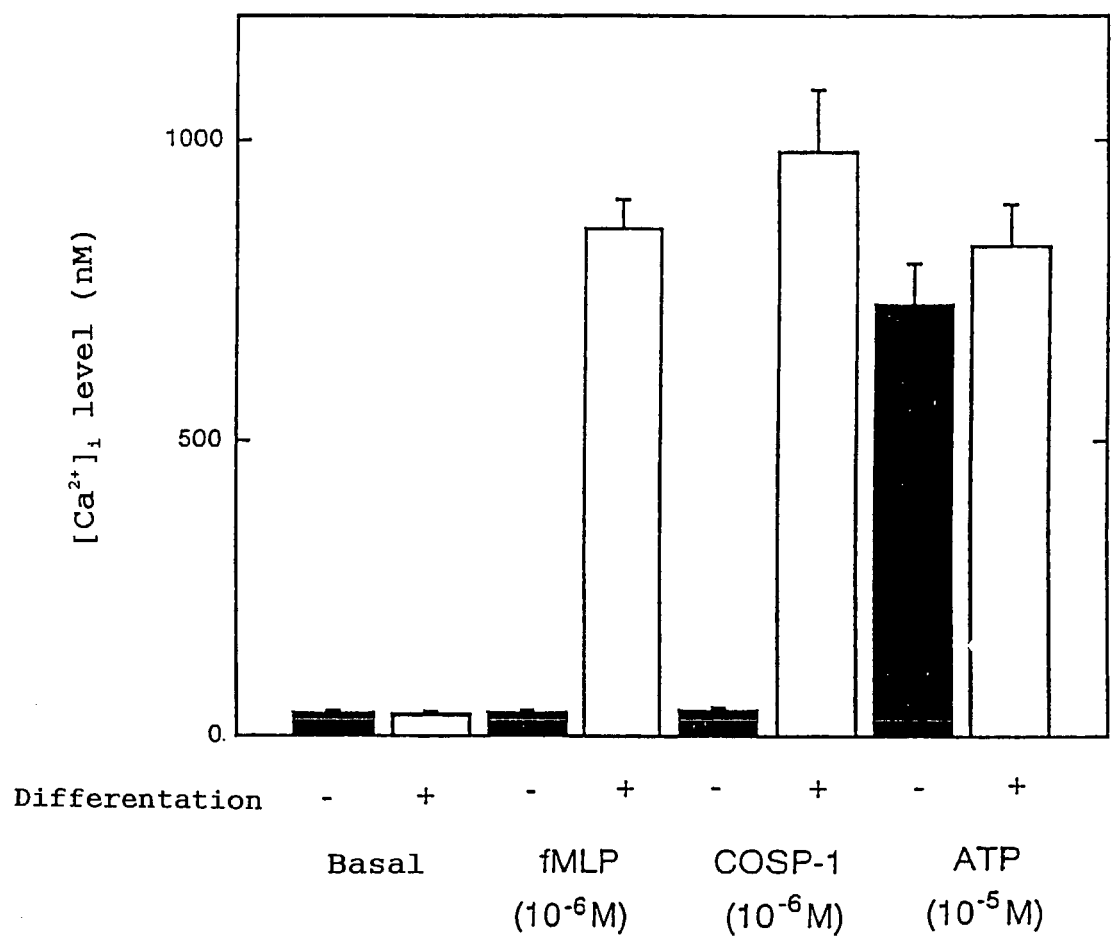
FIG. 4 shows the results of experiments on the effect of the polypeptides on the intracellular $ca^{2+}$ concentrations and the effect of differentiation (Example 7)

The results are shown in FIG. 4. COSP-1 and fMLP increased the intracellular $Ca^{2+}$ concentration of the differentiated HL60 cells (+) but they did not increase that of the undifferentiated the HL60 cells (−). As already reported, ATP increased the intracellular $Ca^{2+}$ concentration in HL60 cells irrespective of whether they were differentiated or not.

Figure 5:
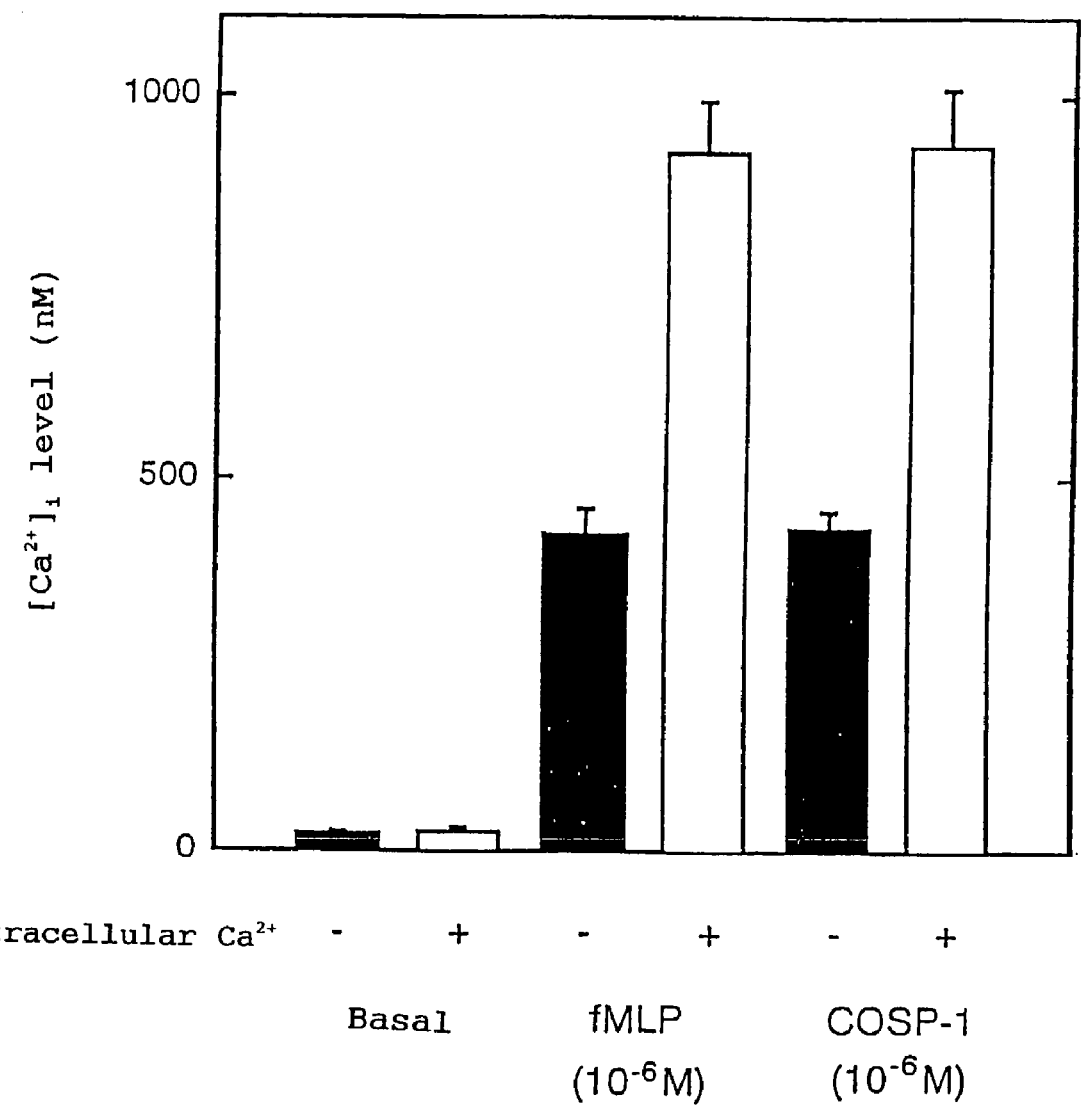
FIG. 5 shows the results of experiments on the effect of polypeptides on the intracellular $ca^{2+}$ concentration as it is also affected by the presence of extracellular calcium (Example 7)

As shown in FIG. 5, upon stimulation with COSP-1 and fMLP, the intracellular $Ca^{2+}$ concentration increased irrespective of whether extracellular $Ca^{2+}$ was present or not. However, the increase was reduced in the absence of $Ca^{2+}$ (−), not in its presence (+). Therefore, it was suggested that upon stimulation with COSP-1 and fMLP, the increase of intracellular $Ca^{2+}$ concentration is caused by both increase in the $Ca^{2+}$ release from the intracellular $Ca^{2+}$ storage and influx of the $Ca^{2+}$ from outside of the cell.

Example 8 (Effect of Treatment with Pertussis Toxin (PTX))

It is known that the fMLP receptors expressed on the differentiated HL60 cells would increase the intracellular $Ca^{2+}$ concentration and cause secretion of degradative enzymes by activating the G protein (PTX sensitive G protein) that is inactivated by PTX treatment. Hence, we investigated how the elevation of the intracellular $Ca^{2+}$ concentration in differentiated HL60 cells and the secretion of β-HA due to stimulation with COSP-1 or are affected by PTX treatment.

(1) Method

PTX treatment was performed in the following way: 16 hours before measurements of the β-HA secreting activity and the intracellular $Ca^{2+}$ concentration, the culture of the differentiated HL60 cells were divided into two; one was treated with PTX at a final concentration of 50 ng/ml; and another was not treated with PTX, but with an equal volume of ultrapure water. For PTX treatment, 50 μg of PTX (purchased from List Biological Laboratories, Inc.) was dissolved in 1 ml of ultrapure water and stored at 2-3° C. before use.

(2) Results and Discussion

Figure 6:
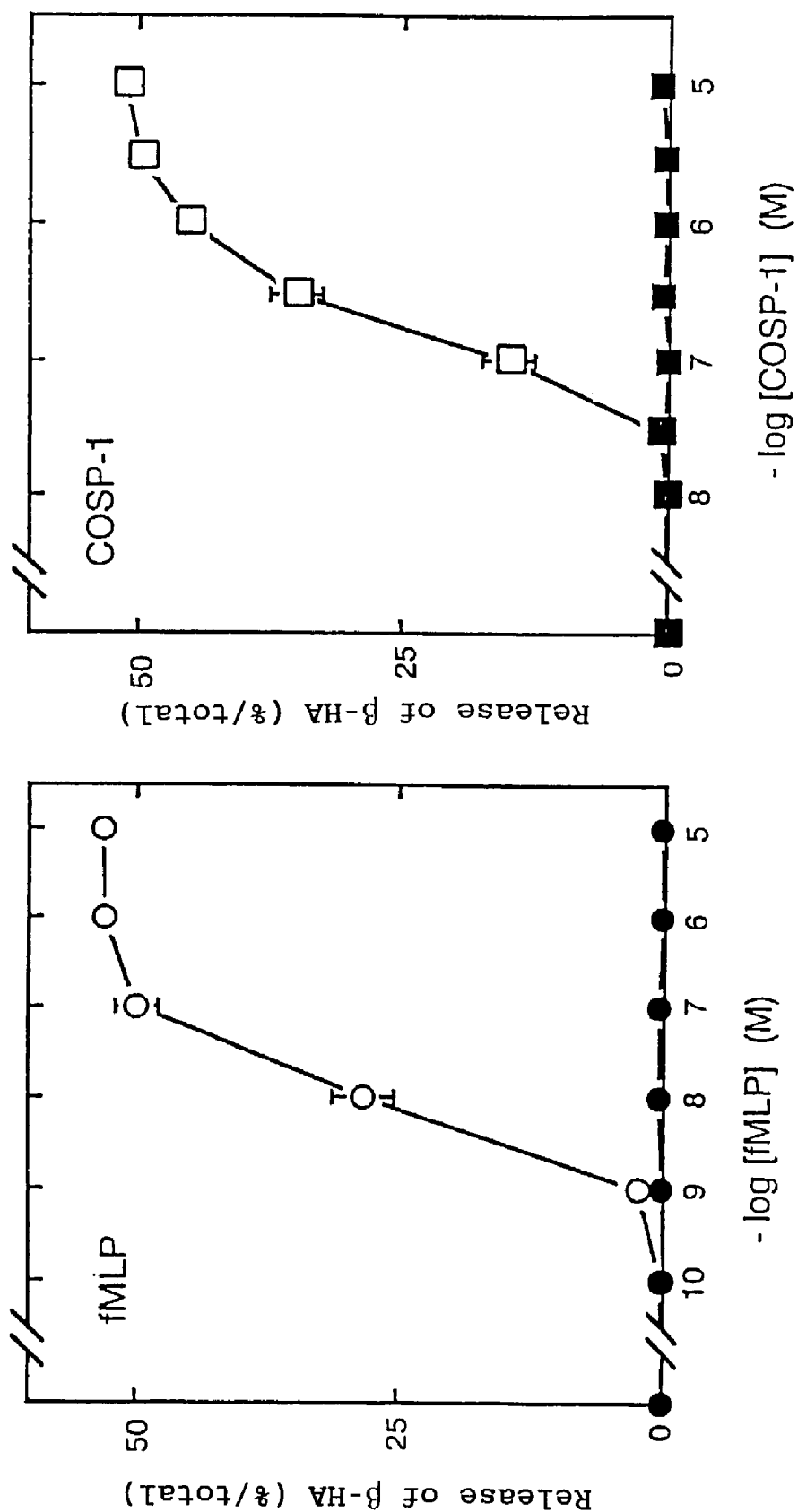
FIG. 6 shows the results of experiments on the effect of PTX treatment on the effect of polypeptides to secrete (Example 8) [● and ■, treated with 50 ng/ml of PTX; ○ and □, treated with ultra-pure water]
Figure 7:
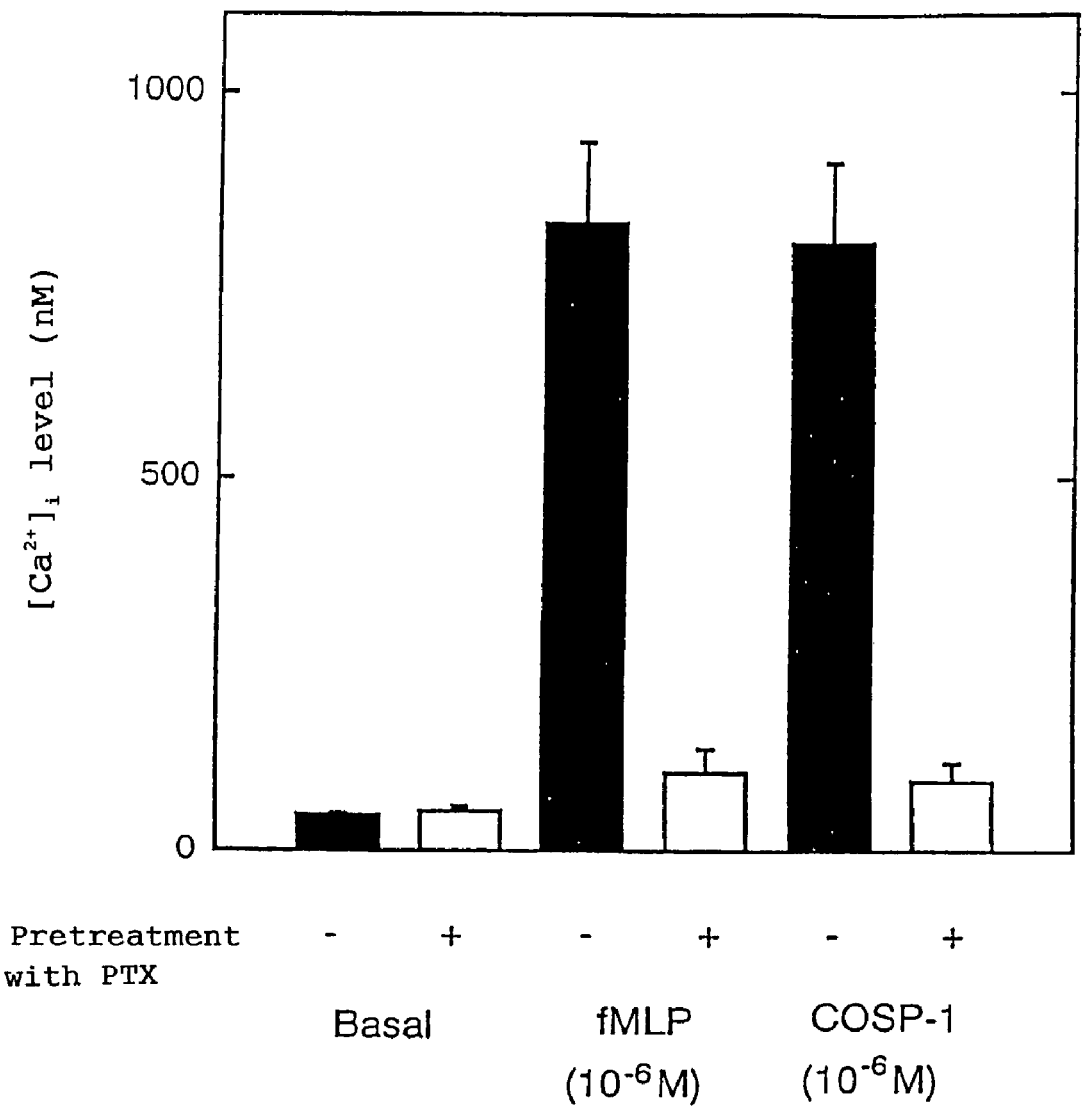
FIG. 7 shows the results of experiments on the effect of PTX treatment on the elevation of intracellular $ca^{2+}$ concentration caused by the polypeptides (Example 8)

The results are shown in FIGS. 6 and 7. The increase in the intracellular $Ca^{2+}$ concentration and the secretion of β-HA upon stimulation with COSP-1 and fMLP was almost completely inhibited by PTX treatment. Therefore, it was suggested that the increase in the intracellular $Ca^{2+}$ concentration and the secretion of β-HA upon stimulation with COSP-1 would be mediated by activation of the receptor(s) which coupled with the PTX sensitive G protein.

Example 9 (Binding Affinity of COSP-1 to the fMLP Receptor(s)

As a result of the investigations on the increase in the intracellular $Ca^{2+}$ concentration and the β-HA secretion upon stimulation with COSP-1, COSP-1 was found to activate the differentiated HL60 cells through very similar mechanisms among experiments (see Examples 6-8). Therefore, in order to investigate the unidentified COSP-1 receptor(s), we first tried to find out how the Boc-MLF, a reported specific inhibitor of fMLP, would affect the COSP-1 promoted secretion of β-HA. As a result, it was found that the COSP-1 promoted secretin of β-HA from the differentiated HL60 cells was significantly suppressed by Boc-MLF treatment (data not shown).

This result suggests the possibility that COSP-1 may bind to the fMLP receptor, so the present inventors further studied the binding of COSP-1 to the fMLP receptor.

(1) Method

The binding study of COSP-1 to the fMLP receptor was done using the differentiated HL60 cells. The differentiated HL60 cells were washed twice with HBHS. Then, the cells were suspended at $3.1 \times 10^7$ cells/ml and this suspension was transferred to tubes ($2.5 \times 10^6$ cells/80 µl) and incubated at 22° C. for 10 minutes. Subsequently, various concentrations of COSP-1 or fMLP (10 µl) were added and incubated at 22° C. for 5 minutes. Thereafter, 10 µl of [$^3$H]fMLP (final concentration at 50 nM) was added and reaction was performed at 22° C. for 60 minutes. By adding 500 µl of ice-cooled PBS-BSA (10 mM phosphate, 120 mM NaCl, 0.5% BSA), the reaction was stopped. The treated cell suspension was then passed through a glass-fiber filter (Whatman GF/C) and the filter was washed three times with ice-cooled PBS-BSA (2 ml) to remove [$^3$H]fMLP not bound to the cells. The glass-fiber filter was dried and a scintillant was added to a solution for radioactivity measurement.

The measurements of binding of the fMLP to the fMLP receptors were expressed as the percentage (%/total) for a maximum binding which was shown as the radioactivity of [$^3$H]fMLP having specific binding to the receptors in the absence of an unlabelled ligand.

(2) Results and Discussion

Figure 8:
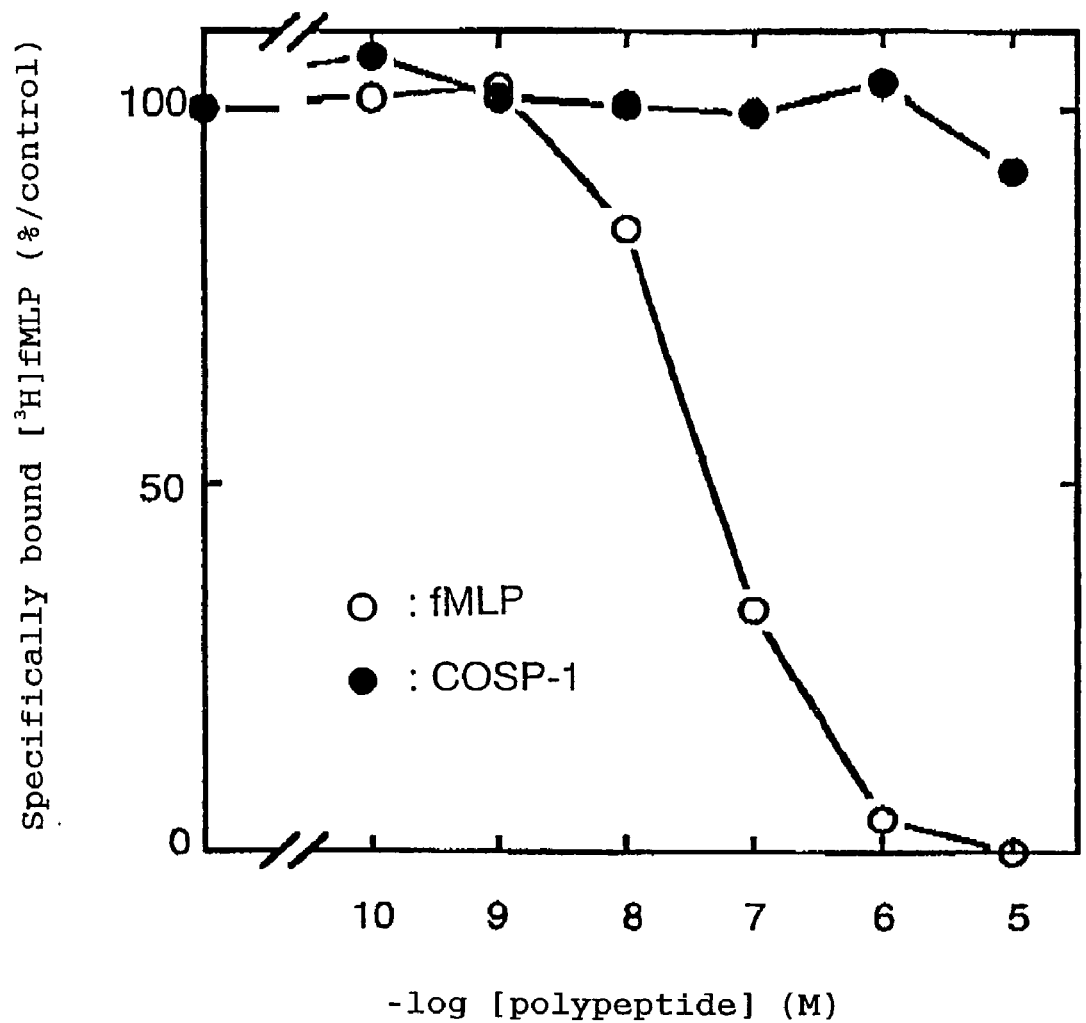
FIG. 8 shows the results of experiments on the binding affinity of COSP-1 to the fMLP receptor (Example 9) [○, fMLP; ●, COSP-1]

The results are shown in FIG. 8. The specific binding between [$^3$H]fMLP and fMLP receptors was inhibited by fMLP in a dose-dependent manner but not by COSP-1 even when its final concentration was reacted to 10 µM. It therefore suggests that COSP-1 would transmit its information in the differentiated HL60 cells via a different receptor than the fMLP receptor.

Example 10 (Activation of G Protein by Peptides)

As it was suggested that COSP-1 would transmit information via a pathway different from the fMLP receptor, we investigated the possibility that COSP-1 could activate the purified G protein. It was done in order to see whether the stimulation by COSP-1 was via a receptor on the surface of cell membrane or a direct activation of the G protein.

(1) Method

G protein (Gi), which is present in neutrophils and involved in single transduction of fMLP, was extracted from the rabbit liver and purified (J. Biol. Chem. 267, 16237-16243, 1992). The purified Gi was reconstituted on a phospholipid membrane, and it was challenged by fCyt b (1-15) or COSP-1. We measured GTPase activity for these stimulations.

(2) Results and Discussion

COSP-1 at 3 µM stimulated the GTPase activity of Gi about 6-fold but fCyt b (1-15) had no stimulating activity even at a concentration of 100 µM.

This result suggests the possibility that COSP-1 would activate neutrophils by directly stimulating the G protein.

Example 11 (Preparation of Monoclonal Antibodies)

Purified COSP-1 (10-100 µg) was bound to a carrier protein and emulsified in an adjuvant. The emulsion was injected intraperitoneally into mice to immunize them. Ten to twelve days later, the mice were given a booster injection once or twice a week. Further, the purified COSP-1 was dissolved in saline and injected intravenously into the mice, from which spleen cells were collected 3-4 days after the injection. The collected cells were fused to mouse myeloma cells NS1 and desired hybridomas between spleen cells and myeloma cells were selected on a HAT medium. We screened the hybridomas that producing the desired antibodies at high concentrations bared on the reactivity with COSP-1.

The selected hybridomas were cultured with Kyokuto E-RDF medium (Kyokuto Seiyaku) supplemented with an additive RD-1 (Kyokuto Seiyaku) in a plastic culture flask (80 cm$^2$, 260 ml, Nunc) for 3-10 days at 37° C., 5% CO$_2$ and 100% humidity. The culture supernatant was concentrated with an ultrafiltration membrane and the desired antibodies were purified following the conventional procedure.

Example 12 (Effects of Human Homologues of COSP-1 and fCyt b (1-15) on Human Derived Neutrophil-Like Cells)

Swine derived COSP-1 and fCyt b (1-15) showed promoting activity of β-HA secretion from the differentiated HL60 cells in a dose-dependent fashion of and attracting activity of the differentiated HL60 cells (see Examples 4 and 5). Since HL60 cells are human-derived cells differentiated from neutrophil-like cells, we scrutinized the activity of the human homologues COSP-1 and fCyt b (1-15) for promoting β-HA secretion from the differentiated HL60 cells and that of promoting the migration of the differentiated HL60 cells. For comparison, the actions of a model peptide fMLP, which is a protein derived from a microorganism-derived protein were investigated.

(1) Method

The activity of the human homologues of COSP-1 and fCyt b (1-15) for promoting β-HA secretion and migration promoting activities were measured following the methods described in Examples 4 and 5, respectively. The activity for β-HA secretion was expressed by the percentage for the maximum amount of secretion upon stimulation with 10 µM of fMLP, whereas the activity for migration was expressed by a chemotaxis index, i.e., the ratio of the number of stimulated migrating cells to that of unstimulated migrating cells.

(2) Results and Discussion

Figure 9:
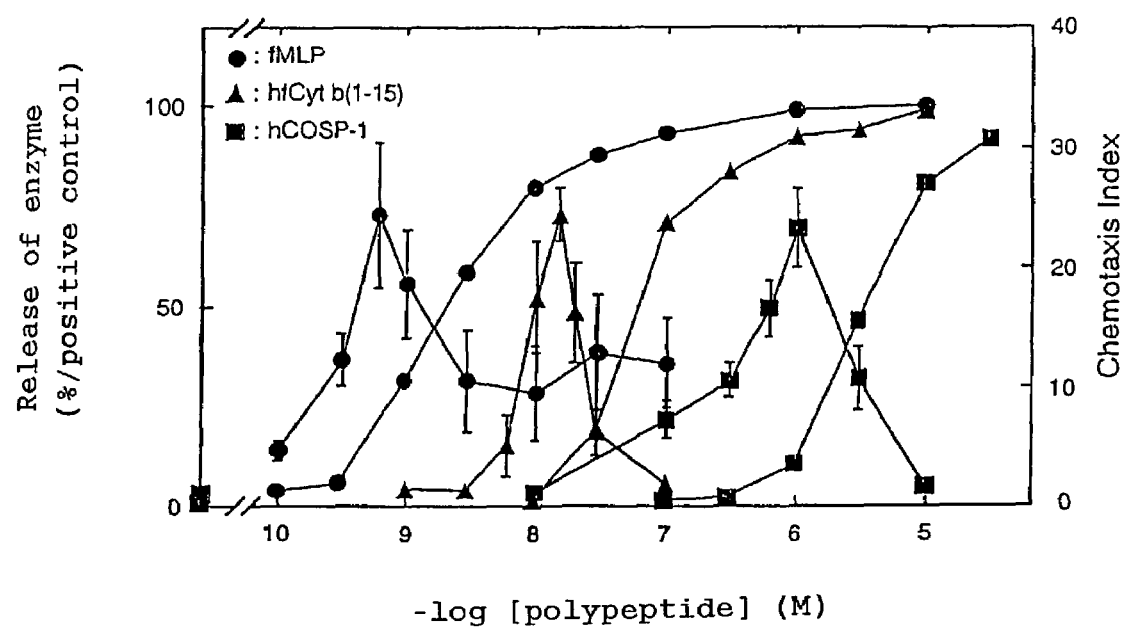
FIG. 9 shows the results of experiments on the effect of fMLP, human COSP-1 and human fCyt b (1-15) on the β-HA secretion and migrating activity of the HL60 cells that are differentiated into neutrophil-like cells (Example 12) [●, fMLP; ▲, fCyt b (1-15); ■, human COSP-1]

The results are shown in FIG. 9.

Both human homologues of COSP-1 (hCOSP-1) and human fCyt b (1-15) (hfCyt b (1-15)) showed the activity of promoting β-HA secretion from the differentiated HL60 cells and of the migration of the differentiated HL60 cells. These activities, however, were not observed in undifferentiated HL60 cells (data not shown).

Characteristic actions were observed in the stimulation with the human homologues. In all cases of fMLP, hCOSP-1 and hfCyt b (1-15), the activity for migration was observed at concentrations lower than the concentration at which the activity for β-HA secretion was exhibited. In the case of fMLP, the activity for migration was also observed at the concentration where the activity of promoting β-HA secretion from the differentiated HL60 cells was observed. On the other hand, in the cases of stimulation with hCOSP-1 and hfCyt b (1-15), the activity for migration was observed only at concentrations lower than the concentrations for causing β-HA secretion and it was desensitized at the concentrations where the activity for β-HA secretion was observed.

From these results, it can be concluded as follows: in the body, hCOSP-1 and hfCyt b (1-15) that diffuse from a site of inflammation will first attract neutrophils (at this stage, the neutrophils are not activated in a point of phagocytosis and production of peroxides). As the concentrations of these peptides increase, the neutrophils are attracted near the site of inflammation, stop migration, are activated at the site and exhibit their actions, such as phagocytosis and peroxide production, whereby they clear harmful substances such as dead cells and damaged cells that exist at the site of inflammation.

Figure 10:
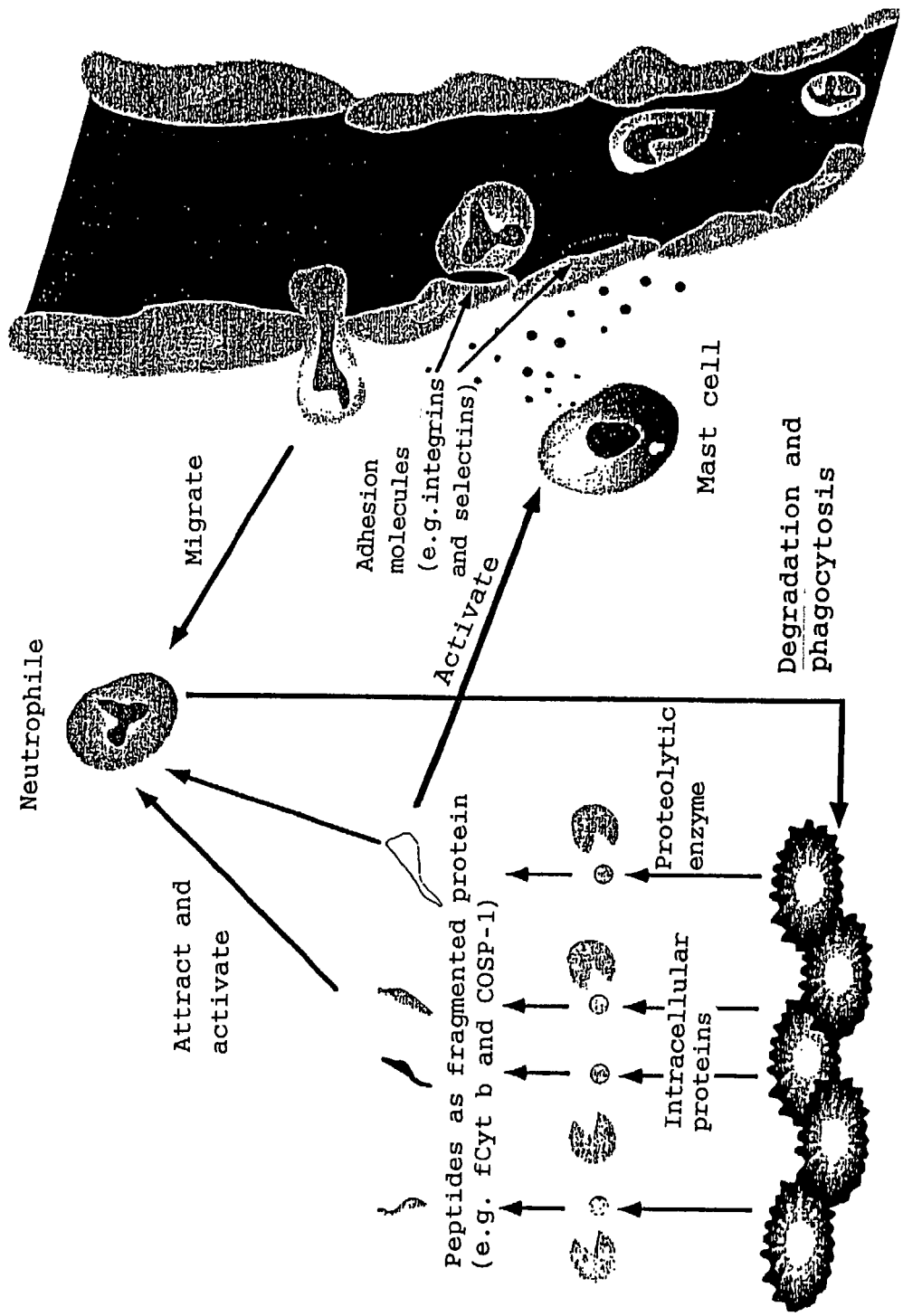
FIG. 10 is a diagrammatic representation of the mechanism of inflammation postulated by the present invention.

Thus, the subject application also offers a new mechanism for the onset of an inflammation that involves hCOSP-1 and hfCyt b (1-15) as outlined below. The mechanism is schematically shown in FIG. 10.

When the tissue injury occurs (a cell is damaged), mitochondria swell up and it causes the protein linkage from the mitochondria. The leaked mitochondrial proteins are fragmented and resulted in generation of peptides, such as hCOSP-1 and hfCyt b (1-15). These peptides are diffused to attract neutrophils to the site of injury. As the neutrophils reach close enough to the site of injury, they stop their movements. At the same time, the neutrophils are activated by these peptides that permit them to secrete various degrading enzymes, to produce various cytokines and active oxygen and to show other actions, such as phagocytosis, whereby they clear the harmful dead cells and damaged cells that exist at the site of injury, as well as the products of these cells.

The invention claimed is:

1. An isolated polypeptide described below under (a), (b) or (c):
   (a) a polypeptide consisting of the amino acid sequence of SEQ ID NO:1;
   (b) a polypeptide consisting of an amino acid sequence which shares at least 90% homology with the amino acid sequence of SEQ ID NO:1 and having neutrophil stimulating activity; or
   (c) a polypeptide consisting of an amino acid sequence identical to the amino acid sequence of said polypeptide (a) or (b) and contains one or more modified amino acids, and having neutrophil stimulating activity.

2. A screening method for identifying a substance which influences the neutrophil stimulating activity of the isolated polypeptide according to claim 1, which comprises the steps of:
   (i) contacting a test substance with the isolated polypeptide according to claim 1; and
   (ii) selecting the substance which influences the neutrophil stimulating activity of said polypeptide by binding to or competing with the binding of said polypeptide.

3. A kit either for determining whether a substance will influence the neutrophil stimulating activity of the polypeptide according to claim 1, which comprises:
   (a) the polypeptide according to claim 1; and
   (b) a container for holding said polypeptide.

4. An isolated polypeptide described below under (a), (b) or (c):
   (a) a polypeptide consisting of the amino acid sequence of SEQ ID NO:3;
   (b) a polypeptide consisting of an amino acid sequence which shares at least 90% homology with the amino acid sequence of SEQ ID NO:3 and having neutrophil stimulating activity; or
   (c) a polypeptide consisting of an amino acid sequence identical to the amino acid sequence of said polypeptide (a) or (b) and contains one or more modified amino acids, and having neutrophil stimulating activity.

5. An isolated polypeptide described below under (a), (b) or (c):
   (a) a polypeptide consisting of the amino acid sequence of SEQ ID NO:4;
   (b) a polypeptide consisting of an amino acid sequence which shares at least 90% homology with the amino acid sequence of SEQ ID NO:4 and having neutrophil stimulating activity; or
   (c) a polypeptide consisting of an amino acid sequence identical to the amino acid sequence of said polypeptide (a) or (b) and contains one or more modified amino acids, and having neutrophil stimulating activity.

6. An isolated polypeptide described below under (a), (b) or (c):
   (a) a polypeptide consisting of the amino acid sequence of SEQ ID NO:5;
   (b) a polypeptide consisting of an amino acid sequence which shares at least 90% homology with the amino acid sequence of SEQ ID NO:5 and having neutrophil stimulating activity; or
   (c) a polypeptide consisting of an amino acid sequence identical to the amino acid sequence of said polypeptide (a) or (b) and contains one or more modified amino acids, and having neutrophil stimulating activity.

7. An isolated polypeptide described below under (a), (b) or (c):
   (a) a polypeptide consisting of the amino acid sequence of SEQ ID NO:1;
   (b) a polypeptide consisting of an amino acid sequence which shares at least 90% homology the amino acid sequence of SEQ ID NO:1 and having G protein stimulating activity; or
   (c) a polypeptide consisting of an amino acid sequence identical to the amino acid sequence of said polypeptide (a) or (b) and contains one or more modified amino acids, and having G-protein stimulating activity.

8. An isolated polypeptide described below under (a), (b) or (c):
   (a) a polypeptide consisting of the amino acid sequence of SEQ ID NO:3;
   (b) a polypeptide consisting of an amino acid sequence which shares at least 90% homology with the amino acid sequence of SEQ ID NO:3 and having G protein stimulating activity; or
   (c) a polypeptide consisting of an amino acid sequence identical to the amino acid sequence of said polypeptide (a) or (b) and contains one or more modified amino acids, and having G-protein stimulating activity.

9. The isolated polypeptide according to any one of claims 1-6, wherein the polypeptide (b) has the activity of promoting the migration of neutrophils or promoting their activation, wherein the activity of promoting the migration is observed at lower polypeptide concentrations than the concentrations which the activity of promoting neutrophil activation is observed.

10. The polypeptide of claim 1, 4, 5, 6, 7 or 8, wherein said polypeptide is (a) or (b).

11. An isolated polypeptide selected from the group consisting of:
    (a) a polypeptide consisting of the amino acid sequence of SEQ ID NO:1;
    (b) a polypeptide consisting of the amino acid sequence of SEQ ID NO:3;
    (c) a polypeptide comprising an amino acid sequence according to amino acid numbers 1-19 of SEQ ID NOS: 1 or 3, wherein said amino acid sequence consist of an amino acid sequence of: Xaa1-Xaa2-Phe-Leu-Xaa3-Pro-Ala-Gly-Trp-Xaa4-Leu-Xaa5-His-Leu-Xaa6-Xaa7-Tyr-Xaa8-Xaa9,
    wherein Xaa1 represents Leu or Val, Xaa2 represents Ser or Thr, Xaa3 represents Ile or Leu, Xaa4 represents Val or Ile, Xaa5 represents Ser or Thr, Xaa6 represents Asp or Glu, Xaa7 represents any amino acid, and each of Xaa8 and Xaa9 represents Lys or Arg,
    wherein said polypeptide has neutrophil stimulating activity, provided that said polypeptide consists of 21-23 amino acids; and
    (d) a polypeptide consisting of amino acid sequence identical to the amino acid sequence of polypeptide (a), (b) or (c) and contains one or more modified amino acids, and having neutrophil stimulating activity.

12. An isolated polypeptide selected from the group consisting of:
    (a) a polypeptide consisting of the amino acid sequence of SEQ ID NO:4;
    (b) a polypeptide consisting of the amino acid sequence of SEQ ID NO:5;
    (c) a polypeptide comprising the amino acid sequence according to SEQ ID NOS: 4 or 5,
    wherein the amino acid sequence consists of: fMet-Thr-Xaa1-Xaa2-Arg-Lys-Xaa3-Xaa4-Pro-Leu-Met-Lys-Xaa5-Ile-Asn,
    wherein Xaa1 represents Asn or Pro, Xaa2 represents Ile or Met, Xaa3 represents Ser or Ile, Xaa4 represents His or Asn and Xaa5 represents Ile or Leu,
    wherein said polypeptide has neutrophil stimulating activity; and
    (d) a polypeptide consisting of an amino acid sequence identical to the amino acid sequence of said polypeptide (a), (b) or (c) and contains one or more modified amino acids, and having neutrophil stimulating activity.

13. An isolated polypeptide selected from the group consisting of:
    (a) a polypeptide consisting of the amino acid sequence of SEQ ID NO:1;
    (b) a polypeptide consisting of the amino acid sequence of SEQ ID NO:3;
    (c) a polypeptide comprising the amino acid sequence according to amino acid numbers 1-19 of SEQ ID NOS: 1 or 3, wherein the amino acid sequence consists of an amino acid sequence of: Xaa1-Xaa2-Phe-Leu-Xaa3-Pro-Ala-Gly-Trp-Xaa4-Leu-Xaa5-His-Leu-Xaa6-Xaa7-Tyr-Xaa8-Xaa9,
    wherein Xaa1 represents Leu or Val, Xaa2 represents Ser or Thr, Xaa3 represents Ile or Leu, Xaa4 represents Val or Ile, Xaa5 represents Ser or Thr, Xaa6 represents Asp or Glu, Xaa7 represents any amino acid, and each of Xaa8 and Xaa9 represents Lys or Arg,
    wherein said polypeptide has G protein stimulating activity, provided that said polypeptide consists of 21-23 amino acids; and
    (d) a polypeptide consisting of an amino acid sequence identical to the amino acid sequence of said polypeptide (a), (b) or (c) and contains one or more modified amino acids, and having G-protein stimulating activity.

14. The polypeptide of claim 11, 12 or 13, wherein said polypeptide is (a), (b) or (c).

* * * * *

UNITED STATES PATENT AND TRADEMARK OFFICE
CERTIFICATE OF CORRECTION

PATENT NO. : 7,285,618 B1
APPLICATION NO. : 10/220849
DATED : October 23, 2007
INVENTOR(S) : Hidehito Mukai et al.

It is certified that error appears in the above-identified patent and that said Letters Patent is hereby corrected as shown below:

In Claim 11, line 15 (at column 30, line numbered 7), change "Xaa5 represents Ser or Thr," to read --Xaa5 represents Ser or Tyr,--.

In Claim 13, line 15 (at column 30, line numbered 53), change "Xaa5 represents Ser or Thr," to read --Xaa5 represents Ser or Tyr,--.

Signed and Sealed this
Twelfth Day of April, 2011

David J. Kappos
*Director of the United States Patent and Trademark Office*

SEQUENCE LISTING

```
<160> NUMBER OF SEQ ID NOS: 7

<210> SEQ ID NO 1
<211> LENGTH: 23
<212> TYPE: PRT
<213> ORGANISM: porcine (heart)

<400> SEQUENCE: 1

Leu Ser Phe Leu Ile Pro Ala Gly Trp Val Leu Ser His Leu Asp His
1               5                   10                  15

Tyr Lys Arg Ser Ser Ala Ala
            20

<210> SEQ ID NO 2
<211> LENGTH: 23
<212> TYPE: PRT
<213> ORGANISM: bovine (heart)
<220> FEATURE:
<221> NAME/KEY: MISC_FEATURE
<222> LOCATION: (1)..(23)
<223> OTHER INFORMATION: 23 residues at the C terminus of bovine heart
      cytochrome C oxidase subunit VIII

<400> SEQUENCE: 2

Leu Ser Phe Leu Leu Pro Ala Gly Trp Val Leu Tyr His Leu Asp Asn
1               5                   10                  15

Tyr Lys Lys Ser Ser Ala Ala
            20

<210> SEQ ID NO 3
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: 21 residues at the C terminus of human
      cytochrome C oxidase subunit VIII

<400> SEQUENCE: 3

Val Thr Phe Leu Leu Pro Ala Gly Trp Ile Leu Ser His Leu Glu Thr
1               5                   10                  15

Tyr Arg Arg Pro Glu
            20

<210> SEQ ID NO 4
<211> LENGTH: 15
<212> TYPE: PRT
<213> ORGANISM: swine
<220> FEATURE:
<221> NAME/KEY: MISC_FEATURE
<222> LOCATION: (1)..(15)
```

```
<223> OTHER INFORMATION: 15 residues at the N terminus of swine
      cytochrome b
<220> FEATURE:
<221> NAME/KEY: misc_feature
<222> LOCATION: (1)..(1)
<223> OTHER INFORMATION: Xaa is a formylated methionyl residue (fMet).

<400> SEQUENCE: 4

Xaa Thr Asn Ile Arg Lys Ser His Pro Leu Met Lys Ile Ile Asn
 1               5                  10                  15

<210> SEQ ID NO 5
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: 15 residues at the N terminus of human
      cytochrome b
<220> FEATURE:
<221> NAME/KEY: misc_feature
<222> LOCATION: (1)..(1)
<223> OTHER INFORMATION: Xaa is a formylated methionyl residue (fMet).

<400> SEQUENCE: 5

Xaa Thr Pro Met Arg Lys Ile Asn Pro Leu Met Lys Leu Ile Asn
 1               5                  10                  15

<210> SEQ ID NO 6
<211> LENGTH: 7
<212> TYPE: PRT
<213> ORGANISM: porcine

<400> SEQUENCE: 6

Lys Ser His Pro Leu Met Lys
 1               5

<210> SEQ ID NO 7
<211> LENGTH: 10
<212> TYPE: PRT
<213> ORGANISM: porcine

<400> SEQUENCE: 7

Lys Ser His Pro Leu Met Lys Ile Ile Asn
 1               5                  10
```